United States Patent [19]
KenKnight et al.

[11] Patent Number: 5,978,705
[45] Date of Patent: Nov. 2, 1999

[54] METHOD AND APPARATUS FOR TREATING CARDIAC ARRHYTHMIA USING AUXILIARY PULSE

[75] Inventors: Bruce H. KenKnight, Maple Grove, Minn.; Raymond E. Ideker, Birmingham, Ala.; Robert S. Booker, III, St. Paul; Stephen J. Hahn, Shoreview, both of Minn.

[73] Assignee: UAB Research Foundation, Birmingham, Ala.

[21] Appl. No.: 09/039,143

[22] Filed: Mar. 13, 1998

Related U.S. Application Data

[63] Continuation-in-part of application No. 08/818,261, Mar. 14, 1997, abandoned.

[51] Int. Cl.$^6$ ................................ A61N 1/39; A61N 1/05
[52] U.S. Cl. ................................................. 607/5; 607/122
[58] Field of Search ........................................ 607/5, 122

[56] References Cited

U.S. PATENT DOCUMENTS

| | | |
|---|---|---|
| 5,107,834 | 4/1992 | Ideker et al. . |
| 5,269,319 | 12/1993 | Schulte et al. . |
| 5,431,683 | 7/1995 | Bowald et al. . |
| 5,464,429 | 11/1995 | Hedberg et al. . |
| 5,522,853 | 6/1996 | Kroll . |
| 5,584,865 | 12/1996 | Hirschberg et al. . |
| 5,609,621 | 3/1997 | Bonner . |
| 5,697,953 | 12/1997 | Kroll et al. . |
| 5,718,718 | 2/1998 | Kroll et al. . |

*Primary Examiner*—William E. Kamm
*Assistant Examiner*—Carl H. Layno
*Attorney, Agent, or Firm*—Myers Bigel Sibley & Sajovec

[57] ABSTRACT

An implantable system for the defibrillation or cardioversion of the heart of a patient in need of such treatment comprises a plurality of primary electrodes, a power supply, and a control circuit. Preferably, at least one auxiliary electrode is also included. The plurality of primary electrodes are configured for delivering a defibrillation pulse along a predetermined current pathway in a first portion of the heart, the current pathway defining a weak field area in a second portion of the heart. The at least one auxiliary electrode is configured for delivering an auxiliary pulse to the a portion of the heart where the primary shock field intensity is at or near a minimum. The control circuit is operatively associated with the primary electrodes, the auxiliary electrode, and the power supply, with the control circuit configured for delivering a cardioversion sequence comprising an auxiliary pulse sufficient to induce a cessation of propagation in the weak field area through the auxiliary electrode, followed by a defibrillation pulse through the primary electrodes delivered during the cessation of propagation in the weak field area.

74 Claims, 10 Drawing Sheets

FIG. 6A
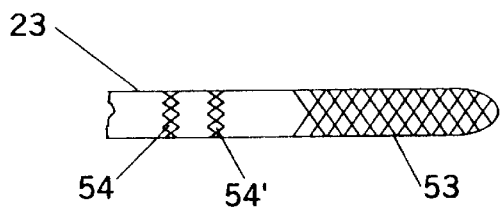
FIG. 6B
FIG. 7
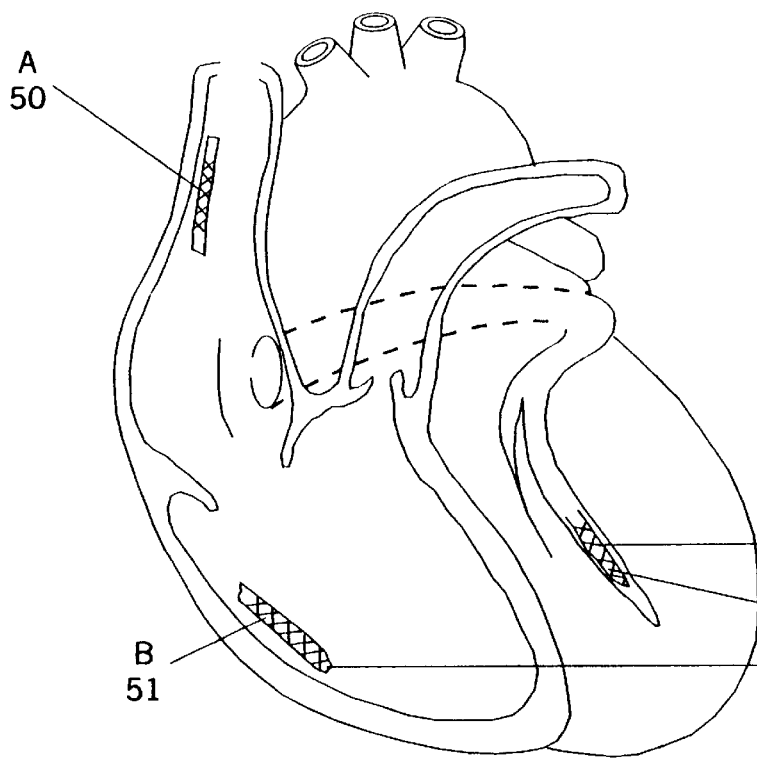
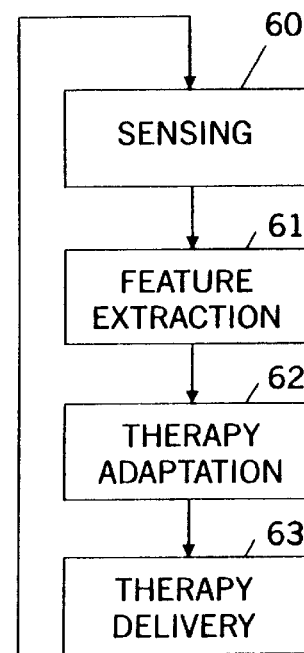

1) B → A+D    C → A+D
2) B → D      C → A

3) B → A+D    C → A+D
4) B → D      C → A

5) B → A+D    C → A+D
6) B → D      C → A

7) B → A+D    C → A+D
8) B → D      C → A

METHOD AND APPARATUS FOR TREATING CARDIAC ARRHYTHMIA USING AUXILIARY PULSE

RELATED APPLICATIONS

This application is a continuation-in-part of copending application Ser. No. 08/818,261, filed Mar. 14, 1997, now abandoned, the disclosure of which is incorporated by reference herein in its entirety.

FIELD OF THE INVENTION

The present invention relates to methods and an implantable apparatus for treating cardiac arrhythmia, particularly ventricular fibrillation.

BACKGROUND OF THE INVENTION

One object in developing implantable defibrillation apparatus has been to lower the shock strength produced by that apparatus so that the size of the shock capacitor, and hence the size of the implantable apparatus itself, can be reduced. Several approaches to achieving this goal have been taken. U.S. Pat. No. 4,780,145 to Tacker et al. discusses the problem with single-pulse defibrillation systems in that the current density between the electrodes is not uniform throughout the ventricles. Tacker describes a sequential-pulse, multiple current pathway defibrillation method in which two defibrillation pulses are delivered along different current pathways.

U.S. Pat. No. 5,536,764 to Adams et al. and U.S. Pat. No. 5,344,430 to Berg et al. both describe implantable defibrillation systems employing two or more successive pulses, but again all pulses are defibrillation pulses. Similarly, U.S. Pat. No. 5,324,309 to Kallok describes successive defibrillation pulses that overlap in time. Adams et al. point out that, after four separate defibrillation attempts, therapy is terminated because conversion thresholds increase with time in a fibrillation episode, and that patients are likely to suffer brain damage after prolonged fibrillation. Hence, it is extremely desirable to increase the likelihood of successful defibrillation on an early attempt: a goal not always consonant with that of decreasing shock strength.

Other implantable defibrillators employ pacing, or pretreatment, pulses. U.S. Pat. No. 5,366,485 to Kroll et al. and U.S. Pat. No. 4,559,946 to Mower et al. both describe defibrillation apparatus in which pacing or pretreatment pulses are delivered through the same electrodes as the defibrillation pulse. U.S. Pat. No. 4,693,253 to Adams and U.S. Pat. No. 5,431,682 to Hedberg both describe defibrillation apparatus in which pacing pulses are delivered after defibrillation. U.S. Pat. No. 5,282,836 to Kreyenhagen et al. describes an atrial defibrillator wherein pacing pulses are delivered through a pacing electrode prior to defibrillation pulses being delivered through a separate set of defibrillation electrodes.

U.S. Pat. No. 5,489,293 to Pless et al. describes an apparatus for treating cardiac tachyarrhythmia which uses a lower voltage defibrillation apparatus by providing a rapid sequence of defibrillation shocks synchronized with sensed sequential cardiac or electrogram events or features during an arrhythmia.

U.S. Pat. No. 5,464,429 to Hedberg et al. describes an apparatus in which a stimulation pulse is delivered through an electrode that ordinarily serves as a pacing electrode, with the stimulation pulse being delivered prior to a defibrillation pulse (the latter being delivered through separate defibrillation electrodes). The stimulation pulse is of a magnitude greater than that of a pacing pulse, but less than that of a defibrillation pulse, and is said to produce a refractory area around the stimulation electrode. However, the stimulation pulse is delivered via an electrode that also serves as a pacing electrode, rather than an electrode specifically positioned in a weak field area of the defibrillation electrodes. The use of a stimulation pulse of a reverse polarity to the first phase of a biphasic defibrillation pulse is not disclosed.

U.S. Pat. No. 5,282,837 to Adams et al. (InControl, Inc.)(see also Divisional application 5,282,837) describes, in FIG. 1 and accompanying text, an atrial defibrillator and method in which a lead 36 is inserted into the coronary sinus so that a first tip electrode 42 is within the coronary sinus adjacent the left ventricle, a second ring electrode 44 is within the coronary sinus beneath the left atrium, and the third electrode 46 within the right atrium or superior vena cava. The first electrode serves as a sensing electrode, the second electrode (still in the coronary sinus) serves as both a sensing and defibrillating electrode, and the third electrode serves as a sensing and defibrillating electrode (see Col. 5 line 57 to Col. 6 line 12).

U.S. Pat. No. 5,433,729 to Adams et al. (corresponds to PCT WO92/18198) is a CIP of Adams '837. Adams '729 describes, in FIG. 9 and accompanying text, a lead system 250 configured in accordance with that described above. A first (right ventricle) lead 252 includes an elongate large surface area electrode 256, a distal or tip sense electrode 258, and a ring or proximal sense electrode 260. Sense electrodes 258, 260 are positioned in and in contact with the wall of the right ventricle, and elongate electrode 256 is in the right atrium. A second (coronary sinus) lead 254 includes a tip, or distal sense electrode 264, a ring or proximal sense electrode 266, and a second elongate, large surface area electrode 262. Distal and proximal sense electrodes 264, 266 are both adjacent the left ventricle within the great vein, and elongate electrode 262 is within the coronary sinus beneath the left atrium. The right ventricle sense electrodes 258, 260 are coupled to inputs 50a, 50b of first sense amplifier 50; the great vein sense electrodes 264, 266 are coupled to inputs 52a, 52b of second sense amplifer 52. This is to provide sensing of the right ventricle and the left ventricle, and the non-coincident sensing of the depolarization activation waves. for synchronizing delivery of energy to the atria (see column 15 line 34 to column 16 line 54; column 5 lines 62–64).

U.S. Pat. No. 5,014,696 to Mehra (Medtronic Inc.) describes an endocardial defibrillation electrode system in which a coronary sinus electrode extending from an area adjacent the opening of the coronary sinus and terminating in the great vein is used in combination with subcutaneous plate electrodes and with right ventricular electrodes. The coronary sinus electrode 78 encircles the left ventricle cavity 86 (Col. 5 lines 50–51; FIG. 5B). It is stated "it is important not to extend the electrode 78 downward through the great vein 80 toward the apex 79 of the heart" (col. 5 lines 28–30). U.S. Pat. No. 5,165,403 to Mehra (Medtronic, Inc.) describes an atrial defibrillation electrode 112 that is located "within the coronary sinus and the great cardiac vein."

U.S. Pat. No. 5,099,838 to Bardy (filed Dec. 15, 1988; Medtronic, Inc.) describes a defibrillation electrode in the great vein that is used in combination with subcutaneous plate electrodes and with right ventricular electrodes (col. 1 line 65 to col. 2 line 2). With respect to the great vein electrode, it is stated at column 5, lines 20–33 therein: "When so mounted, the elongate defibrillation electrode 78 extends from a point adjacent the opening of the coronary sinus 74 and into the great vein 80. This provides a large surface area defibrillation electrode which is generally well spaced from the ventricular defibrillation electrode 74 and provides good current distribution in the area of the left ventricle 77. It is desireable to extend the electrode 78 around the heart as far as possible. However, it is important not to extend the electrode 78 downward through the great vein 80 toward the apex 79 of the heart, as this will bring the coronary sinus and right ventricular electrodes into close proximity to one another, interfering with proper current distribution. U.S. Pat. No. 5,193,535 to Bardy (filed Aug. 27, 1991) also describes a great vein electrode. At column 7, lines 31–35, it is stated: "The coronary sinus lead is provided with an elongated electrode located in the coronary sinus and great vein region at 112, extending around the heart until approximately the point at which the great vein turns downward toward the apex of the heart."

U.S. Pat. No. 5,431,683 to Bowald et al. (Siemens) describes a ventricular defibrillation electrode system in which on electrode is placed through the coronary sinus into a peripheral vein of the heart. The term "peripheral vein" is defined therein as to encompass "the venous side of the coronary vessels running between the base and the apex of the heart. The [sic] include the middle and small cardiac veins, and the portion of the great cardiac vein which runs between the base and apex of the heart. The definition of "peripheral veins" used herein, therefore, excludes that portion of the great cardiac vein which runs along the base plane of the heart, which has been used [as] a site for electrode placement in prior art electrode systems." The electrodes are in the shape of a helix to apply pressure against the inner wall (col. 4, lines 14–17), with blood being able to flow unobstructed through the interior of the helix (column 4, lines 46–48)(See also U.S. Pat. No. 5,423,865 to Bowald). Such stent-type electrodes can be difficult to adjust or remove. Only a simple shock pattern is described in Bowald, and efficacious electrode configurations and shock patterns are neither suggested nor disclosed.

U.S. Pat. No. 5,690,686 to Min et al. (Medtronic Inc.) describes an atrial defibrillation method in which a coronary sinus/great vein electrode is coupled to a right atrial/superior vena cava electrode and a subcutaneous electrode in the form of the housing of an implantable defibrillator. The device is stated to be preferably practiced as a combined atrial/ventricular defibrillator (col. 2, lines 26–35).

In view of the foregoing, a first object of the invention is to provide an implantable system for treating cardiac arrythmia that does not require invasion of the chest cavity for the placement of epicardial electrodes.

A second object of the invention is to provide an implantable cardioversion system wherein the probability of successful cardioversion on administration of the first cardioversion pulse is enhanced, particularly in the case of ventricular fibrillation.

A third object of the invention is to provide an implantable system for treating cardiac arrythmia that can enable reduction of cardioversion, and particularly defibrillation, shock strength.

SUMMARY OF THE INVENTION

A first aspect of the present invention is an implantable system for the defibrillation or cardioversion of a patient's heart. The system comprises a plurality of primary electrodes, a power supply, and a control circuit. The plurality of primary electrodes are configured for delivering a defibrillation pulse along a predetermined current pathway in a first portion of the heart, with a first one of the primary electrodes configured for positioning through the coronary sinus and within a vein on the surface of the left ventricle of the heart. The control circuit is operatively associated with the power supply and the primary electrodes, and the control circuit is configured for delivering a defibrillation pulse through the primary electrodes.

A second aspect of the present invention is an implantable system for the defibrillation or cardioversion of the heart of a patient in need of such treatment. The system comprises a plurality of primary electrodes, at least one auxiliary electrode, a power supply, and a control circuit. The plurality of primary electrodes are configured for delivering a defibrillation pulse along a predetermined current pathway in a first portion of the heart, the current pathway defining a weak field area in a second portion of the heart. The weak field area is the portion of the heart where the defibrillation shock field intensity is at or near a minimum. At least one auxiliary electrode is configured for delivering an auxiliary pulse to the weak field area. The control circuit is operatively associated with the primary electrodes, the auxiliary electrode, and the power supply, with the control circuit configured for delivering a cardioversion sequence comprising an auxiliary pulse sufficient to alter transmembrane potential in the weak field area through the auxiliary electrode, followed by a defibrillation pulse through the primary electrodes delivered while the electrophysiological effects imparted by the auxiliary pulse in the weak field area are present.

One preferred embodiment of the foregoing apparatus is an implantable system for the defibrillation of the ventricles of the heart of a patient in need of such treatment. The system comprises a plurality of primary electrodes, at least one auxiliary electrode, a power supply, and a control circuit. The plurality of primary electrodes are configured for delivering a defibrillation pulse along a predetermined current pathway in a first portion of the heart, the current pathway defining a weak field area in a second portion of the heart. At least one auxiliary electrode is configured for delivering an auxiliary pulse to the weak field area, with the at least one auxiliary electrode configured for positioning through the coronary sinus and in a vein on the surface of the left ventricle of the heart. The control circuit is operatively associated with the primary electrodes, the at least one auxiliary electrode, and the power supply, the control circuit configured for delivering a cardioversion sequence comprising a monophasic auxiliary pulse through the auxiliary electrode, followed by a biphasic defibrillation pulse through the primary electrodes, with the defibrillation pulse delivered within 20 milliseconds after the auxiliary pulse, and with the first phase of the defibrillation pulse in opposite polarity to the auxiliary pulse.

Primary electrodes and auxiliary electrodes may be carried by one or more transvenous leads, and the implantable defibrillator housing may carry an electrode on the outer surface thereof.

In alternate embodiments of the invention, the order of the cardioversion sequence may be reversed, so that the sequence comprises a defibrillation pulse through the primary electrodes, followed by an auxiliary pulse sufficient to alter transmembrane potential in the weak field area through the auxiliary electrode while the electrophysiological effects imparted by the primary pulse in the weak field area are present. Parameters for the two shocks (time intervals, shock strength and polarities) are otherwise the same. However, when the auxiliary pulse is delivered after the primary, or defibrillation, pulse, the auxiliary pulse is preferably a biphasic pulse (in this case, the primary pulse may optionally be monophasic).

A still further object of the present invention is an electrode lead useful for the cardioversion or defibrillation of a patient's heart. The lead comprises an elongate transveneous electrode lead having a distal end portion, with the lead configured for positioning the distal end portion within the right atrial appendage or the right ventricular outflow track, and a primary electrode connected to the electrode lead and positioned on the distal end portion thereof.

The foregoing and other objects and aspects of the present invention are described in greater detail in the drawings herein and the specification set forth below.

BRIEF DESCRIPTION OF THE DRAWINGS

FIGS. 6a and 6b illustrate endocardial electrodes that may be used to carry out the apparatus illustrated in FIG. 5;

FIG. 7 schematically illustrates how an apparatus of the present invention is modified to control the therapy delivered;

DETAILED DESCRIPTION OF THE INVENTION

Figure 1:
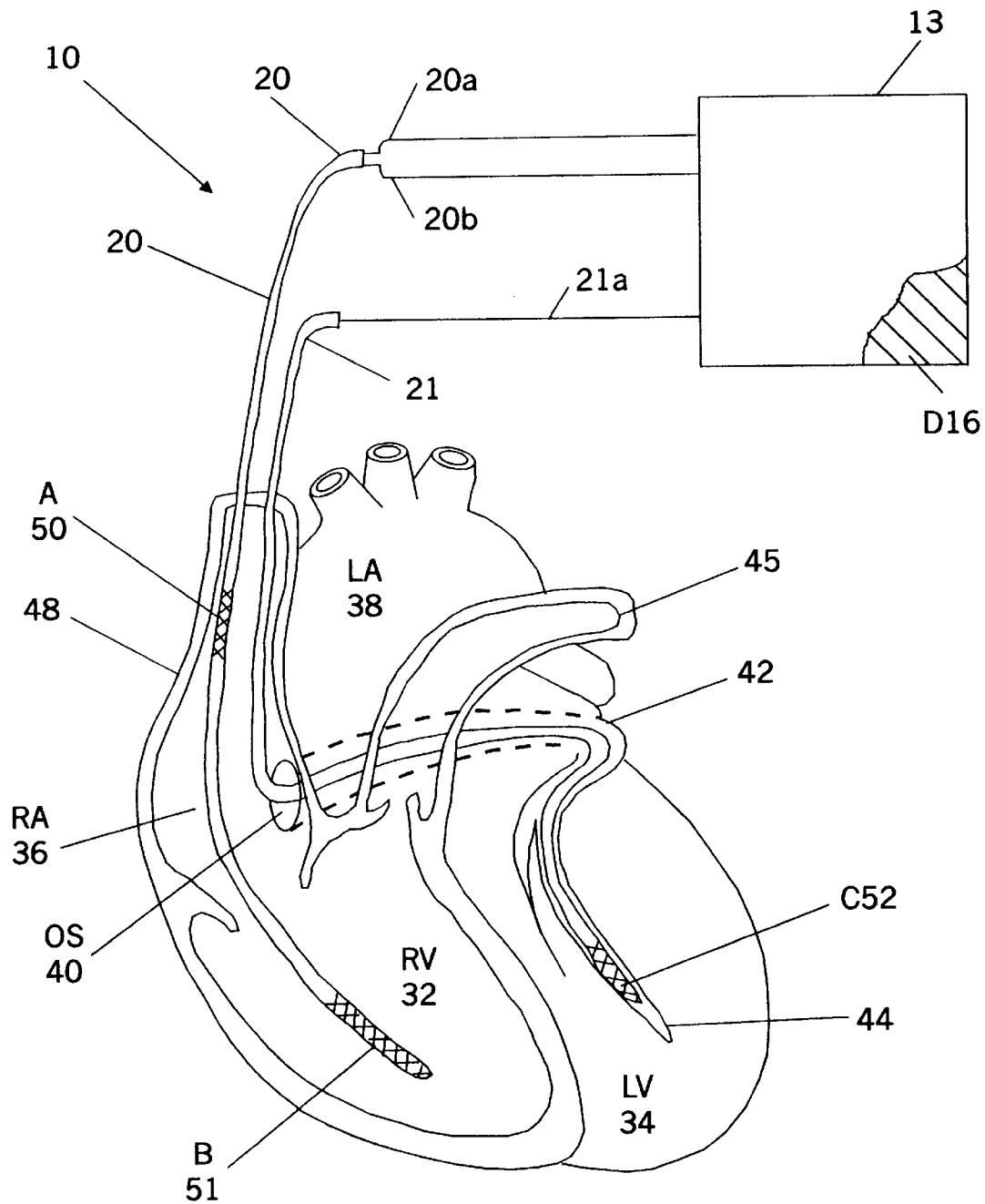
FIG. 1 illustrates a preferred set of electrode placements in an apparatus for carrying out the present invention.

The present invention may be used to treat all forms of cardiac tachyarrythmias, including ventricular fibrillation, with defibrillation (including cardioversion) shocks or pulses. The treatment of polymorphic ventricular tachycardia and ventricular fibrillation are particularly preferred.

Anatomically, the heart includes a fibrous skeleton, valves, the trunks of the aorta, the pulmonary artery, and the muscle masses of the cardiac chambers (i.e., right and left atria and right and left ventricles). The schematically illustrated portions of the heart 30 illustrated in FIG. 1 includes the right ventricle "RV" 32, the left ventricle "LV" 34, the right atrium "RA" 36, the left atrium "LA" 38, the superior vena cava 48, the coronary sinus "CS" 42, the great cardiac vein 44, the left pulmonary artery 45, and the coronary sinus ostium or "os" 40.

The driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers, and then traveling into the atria and subsequently passing through the AV node and, after a slight delay, into the ventricles.

The beginning of a cardiac cycle is initiated by a P wave, which is normally a small positive wave in the body surface electrocardiogram. The P wave induces depolarization of the atria of the heart. The P wave is followed by a cardiac cycle portion which is substantially constant with a time constant on the order of 120 milliseconds ("ms").

Various embodiments of the present invention can be illustrated with reference to FIG. 1. The defibrillator 10 of FIG. 1 includes an implantable housing 13 that contains a hermetically sealed electronic circuit 15 (see FIG. 2). The housing includes an electrode comprising an active external portion 16 of the housing, with the housing 13 preferably implanted in the left or right thoracic region of the patient (e.g., subcutaneously or submuscularly, in the left or right pectoral region, or subcutaneously or submuscularly in the left or right (preferably left) abdominal region; the left pectoral region is most preferred) in accordance with known techniques as described in G. Bardy, U.S. Pat. No. 5,292, 338.

The system includes a first catheter 20 and a second catheter 21, both of which are insertable into the heart (typically through the superior or inferior vena cava) without the need for surgical incision into the heart. The term "catheter" as used herein includes "stylet" and is also used interchangeably with the term "lead". Each of the catheters 20, 21 contains electrode leads 20a, 20b, 21a, respectively.

As illustrated in FIG. 1, the system includes an electrode A; 50 that resides in the superior vena cava or innominate vein, an electrode B; 51 positioned in the right ventricle, and an electrode C; 52 positioned within a vein on the postero lateral surface of the left ventricle (e.g., in the apical third of the posterior cardiac vein or the apical half of the great cardiac vein). The active external portion of the housing 16 serves as a fourth electrode D. Designations "A" through "D" herein refer to electrodes in the aforesaid positions.

Electrode C may be a hollow electrode to allow the flow of blood through the electrode (e.g., a stent-type electrode that engages the vessel wall) when positioned in the vein, or may be a solid electrode configured (that is, of a shape and size) to allow the flow of blood around the electrode when positioned within the vein. A solid electrode is preferred. Electrode C may be positioned entirely within a vein on the postero-lateral surface of the left ventricle, or may also extend into the coronary sinus (as in the case of an elongate electrode).

The position of electrode C may be achieved by first engaging the coronary sinus with a guiding catheter through which a conventional guidewire is passed. The tip of the torqueable guidewire is advanced under fluoroscopic guidance to the desired location. The lead 21 on which electrode C is mounted passes over the guidewire to the proper location. The guidewire is withdrawn and electrode C is incorporated into the lead system. Such an electrode is considered a solid-type electrode herein.

Figure 2:
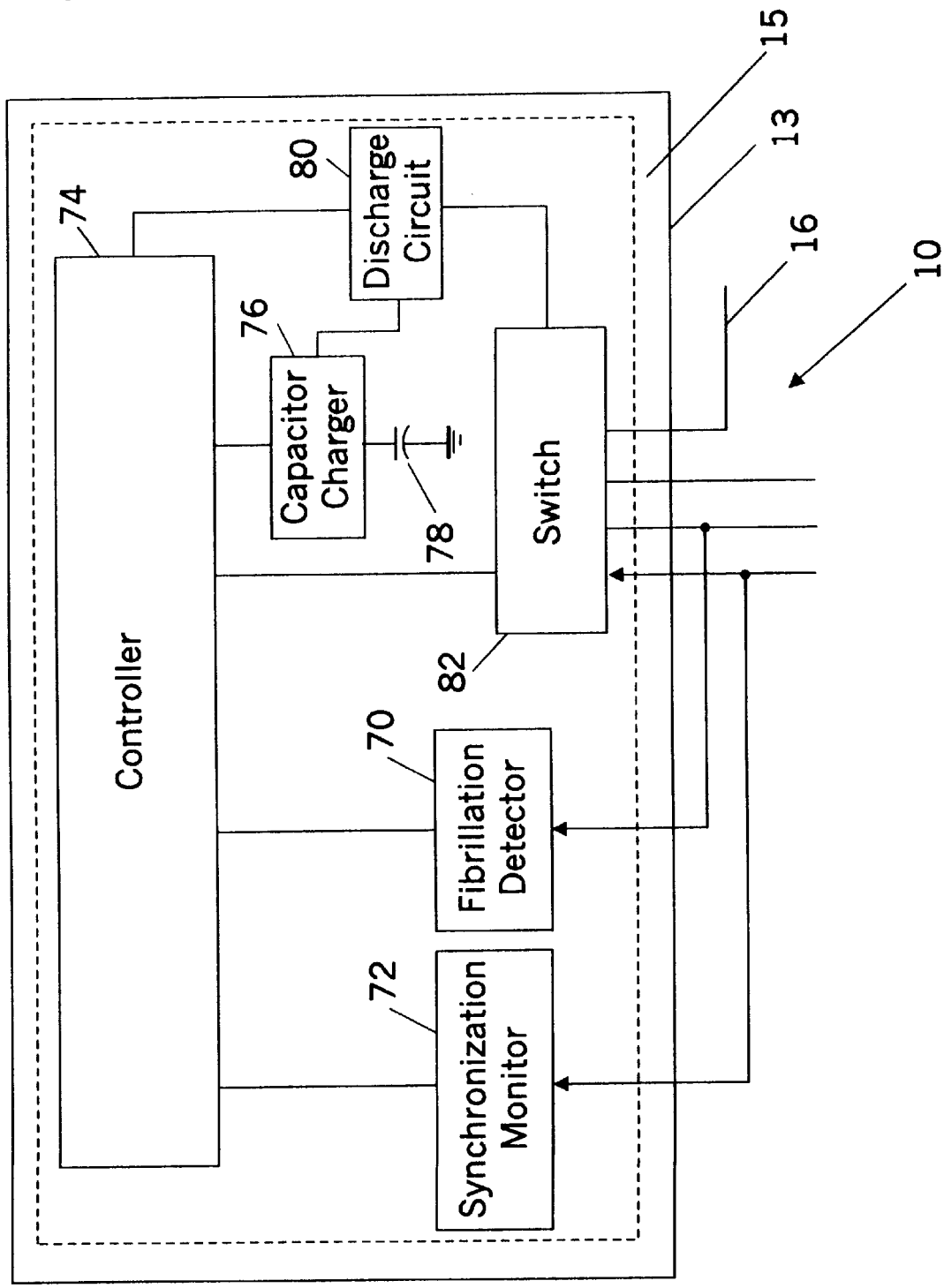
FIG. 2 schematically illustrates the control circuitry employed in an apparatus of the present invention.

FIG. 2 illustrates one example of an implantable housing 13 containing an electronic circuit 15, which includes one or more amplifiers (not shown) for amplifying sensed cardiac signals. The amplified signals are analyzed by an detector 70 which determines if ventricular fibrillation (or other arrythmia, depending on the specific treatment for which the device is configured) is present. The detector 70 may be one of several known to those skilled in the art. Although, as illustrated, a sensing signal is provided by the electrode A 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

The defibrillation electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 15 also includes a cardiac cycle monitor ("synchronization monitor 72") for providing synchronization information to the controller 74. As discussed below, the synchronization is typically provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

Numerous configurations of capacitor and control circuitry may be employed. The power supply may include a single capacitor, and the control circuit may be configured so that both the auxiliary pulse and the defibrillation pulse are generated by the discharge of the single capacitor. The power supply may include a first and second capacitor, with the control circuit configured so that the auxiliary pulse is generated by the discharge of the first capacitor and the defibrillation pulse is generated by the discharge of the second capacitor. In still another embodiment, the power supply includes a first and second capacitor, and the control circuit may be configured so that the auxiliary pulse is generated by the discharge (simultaneous or sequential) of both the first and second capacitors, and the defibrillation pulse likewise generated by the discharge of the first and second capacitors.

Figure 3:
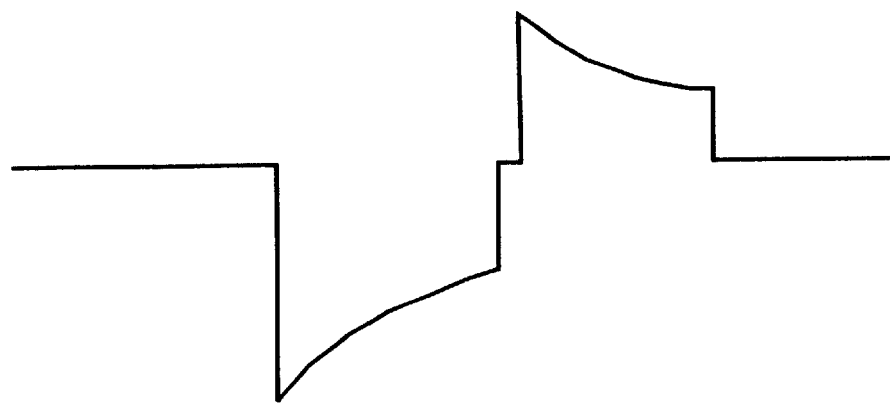
FIG. 3 illustrates a waveform that may be used to carry out the present invention.
Figure 4:
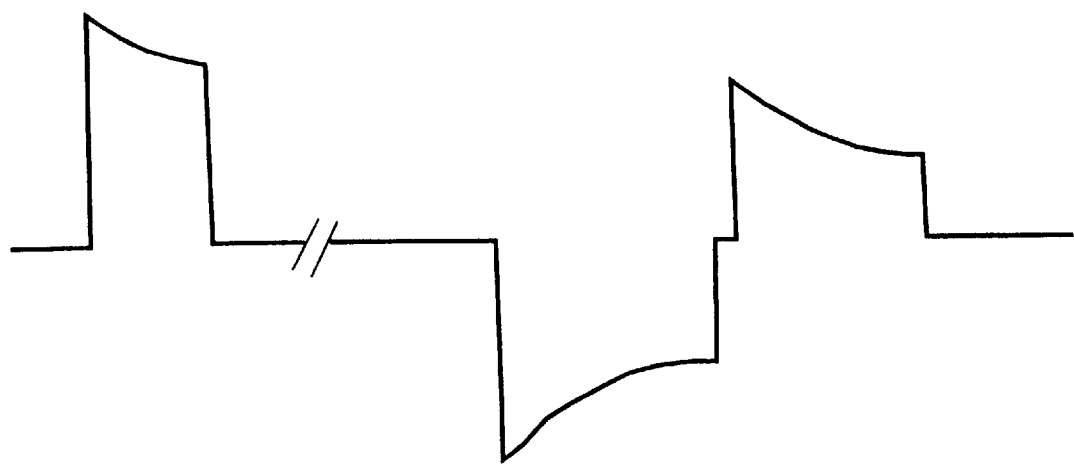
FIG. 4 illustrates a preferred waveform that may be used to carry out the present invention.

One defibrillation waveform that may be used to carry out the present invention is illustrated in FIG. 3, which shows a schematic illustration of a biphasic truncated exponential waveform. While a variety of different waveforms can be used, as discussed herein, surprisingly good results are achieved when an auxiliary pulse is delivered prior to the primary, or defibrillation, pulse, with the auxiliary pulse being delivered along a different current pathway. A particularly surprising finding was that better results can be achieved when the auxiliary pulse is of an opposite polarity than the first phase of the defibrillation pulse. Such a biphasic truncated exponential waveform primary pulse with a monophasic auxiliary pre-pulse is illustrated in FIG. 4. The foregoing waveforms can be modified in ways that will be apparent to those skilled in the art (e.g., a chopped waveform can be delivered; the waveform can be time-based or fixed tilt; etc).

The auxiliary pulse may be from 0.5 or 1 to 5 or 10 milliseconds in duration, with a 2 millisecond pulse currently preferred. The time interval from the end of the auxiliary pulse to the leading edge of the primary pulse may be from 1 or 2 milliseconds to 10, 15 or 20 milliseconds, with a delay of about 5 milliseconds currently preferred.

The optimal auxiliary-to-primary interval may differ depending on the type of rhythm or condition of the myocardial tissue at the time the therapy is applied. Therefore, the control circuitry may also be configured to sense a characteristic of the cardiac rhythm (e.g., an activation interval or a dynamical pattern of consecutive activation intervals) and then select an optimum auxiliary-to-primary shock time interval (e.g., from a look up table stored in a microprocessormemory).

The percent tilt of the primary pulse and the auxiliary pulse may each be from 10, 20 or 30 percent up to 50 or 60 percent. Percent tilt=$(V_o-V_f \times 100)/V_o$, where $V_o$ is the initial voltage and $V_f$ is the final voltage of the pulse. $V_f$ refers to the final voltage of the final phase of the shock where the shock sequence has multiple phases.

In general, the control circuit is configured so that the auxiliary pulse is not more than 40% or 50% of the peak current and not more than 20% or 30% of the delivered energy (in Joules) of the defibrillation pulse. In a preferred embodiment, the trailing edge voltage of the auxiliary pulse is equal (±10 Volts) to the leading edge voltage of the defibrillation pulse. Particular voltage, current, and energy outputs will depend upon factors such as the condition of the tissue and the particular disorder being treated. In general, the auxiliary pulse may have a peak voltage of from 20 or 30 volts to 200 or 250 volts, with a peak voltage range of 50 to 150 volts preferred. The energy of the auxiliary pulse may be from 0.01 or 0.05 to 1 or 2 Joules. The energy of the defibrillation pulse may be from 5 or 10 Joules to 30, 40 or 50 Joules. An object of the instant invention is to enable the reduction of the size of the implantable defibrillator, which is made possible by defibrillation pulse energy ranges as described. Thus, a further aspect of the present invention is an implantable defibrillator comprising a housing and a power supply contained within the housing, and a control circuit contained within the housing and operatively associated with the power supply. The control circuit is configured for delivering a cardioversion sequence as described above. Based on the ranges above, the maximum storage capacity of the capacitor in the power supply may be from 5.01 to 52 Joules, and is most preferably from 10 or 15 to 20 Joules. Thus the housing for such a power supply preferably has a volume less than 35 cubic centimeters (but typically at least 5 cubic centimeters).

Without wishing to be bound to any particular theory for the preferred waveforms described above, it appears that the auxiliary pulse, which is of a magnitude greater than pacing pulses but less than a defibrillation pulse, is sufficient to affect/substantially alter the intrinsic patterns of recovery of excitability and thereby momentarily yield localized cessation of propagation by inactivating sodium ion conductance channels via elevation of the transmembrane potential. Importantly, the tissue portions affected by the auxiliary pulse is tissue in a weak field area for the primary, or defibrillation, pulse. The weak field area affected by the auxiliary pulse should be selected to include the weakest field area of the primary pulse. In a preferred embodiment, the weak field area is generally the left lateral aspect of the left ventricle, extending from the apex to the base thereof.

Numerous different embodiments of the implantable system of the present invention can be implemented with the apparatus of FIGS. 1 and 2 and the waveforms of FIGS. 3 and 4, depending on the specific configuration of the control circuitry for the use and pairing of particular electrodes. Specific examples are discussed below.

Table 1 illustrates a first embodiment of the invention. After a tachyarrhythmic condition is detected and reconfirmed by algorithms running in the controller 74, therapy in the form of an electrical shock of FIG. 3 is applied to the heart by discharging capacitor 78. A preferred pairing of electrodes for this embodiment is illustrated in Table 1 below. In all tables herein, a "+" indicates that the electrodes are electrically common, and an "→" indicating current flow (which may be reversed).

TABLE 1

| Electrode Pairings |
| --- |
| Primary Pulse |
| B + C –> A + D |

Table 2 illustrates a second embodiment of the invention. This embodiment introduces the use of an auxiliary pulse, with four possible configurations being shown in FIG. 4. The auxiliary pulse is delivered through a different set of electrodes than the primary, or defibrillation, pulse.

TABLE 2

| Electrode Selection | |
| --- | --- |
| Auxiliary Pulse | Primary Pulse |
| C –> D | A –> B |
| A –> B | C –> D |
| C –> A | B –> C |
| B –> D | C –> A |
| C –> D | B –> D |
| C –> B | B –> A + D |

In one embodiment of an apparatus configured according to Table 2, the control circuitry is configured so that only one capacitor is employed to deliver both pulses, and that the different sets of electrodes are switched in and out of the discharge circuit to achieve the therapeutic effect. In this embodiment, the trailing edge of the auxiliary pulse is equal to the leading edge of the primary pulse.

In another embodiment of an apparatus configured according to Table 2, the control circuitry is configured so that the auxiliary pulse and the primary pulse arise from separate capacitors. For example, if the design goal is to control the time constant of the capacitor discharge waveform (time constant is the product of the resistance and the capacitance) and assuming further that the resistance to the shock (ratio of voltage to current) along the auxiliary pathway is two-fold higher than along the primary pathway, then the capacitance of the auxiliary capacitor could be half that of the primary shock capacitor. Further, with a two capacitor implementation, the relative strength of the pulses can be made independent. In this way, the minimum auxiliary shock strength can be applied that produces the synergistic action between the auxiliary and primary shocks, thereby minimizing the shock strength requirements for effective defibrillation.

Figure 5:
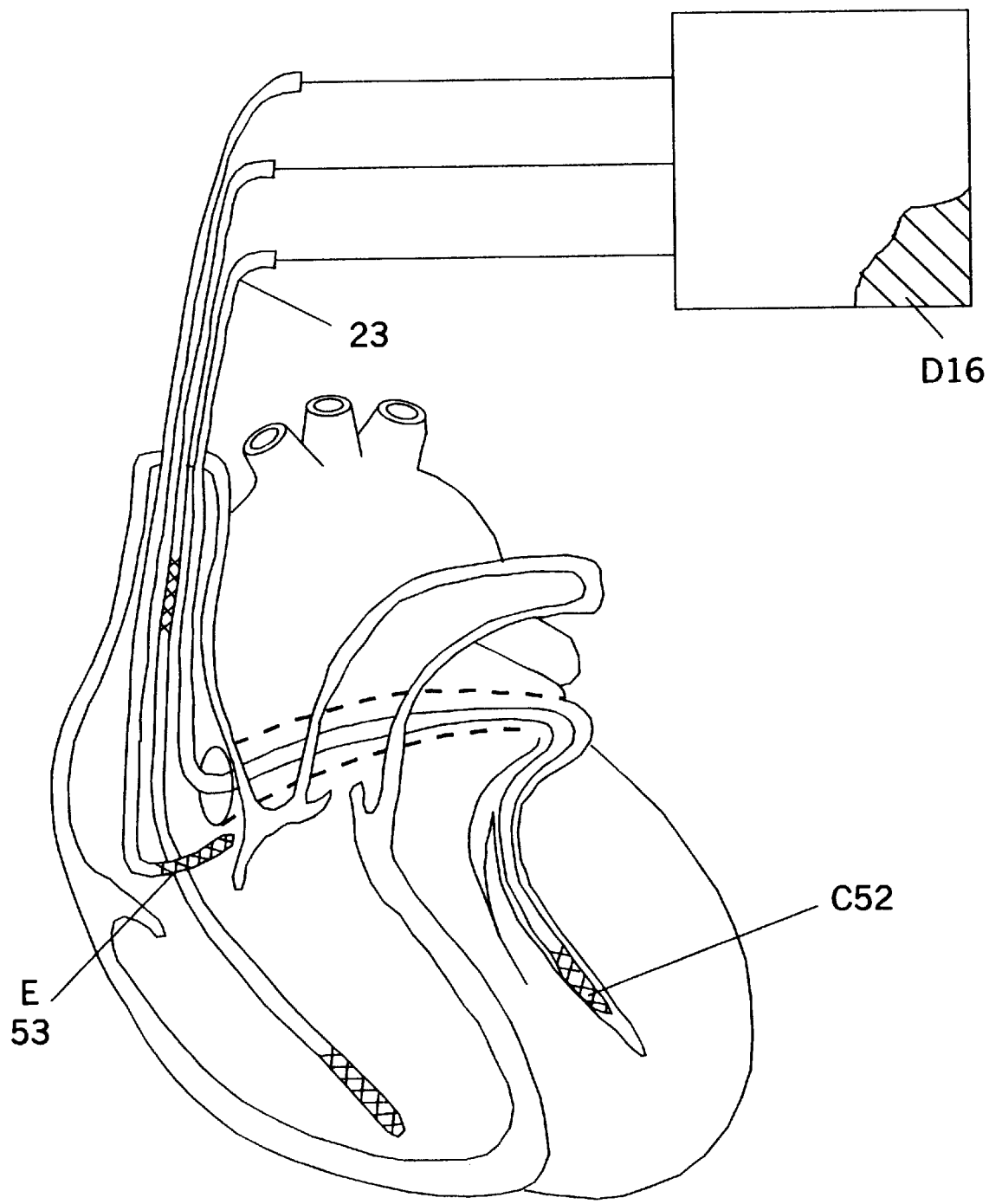
FIG. 5 illustrates an alternate set of cardiac electrode placements in an apparatus for carrying out the present invention.
Figure 8:
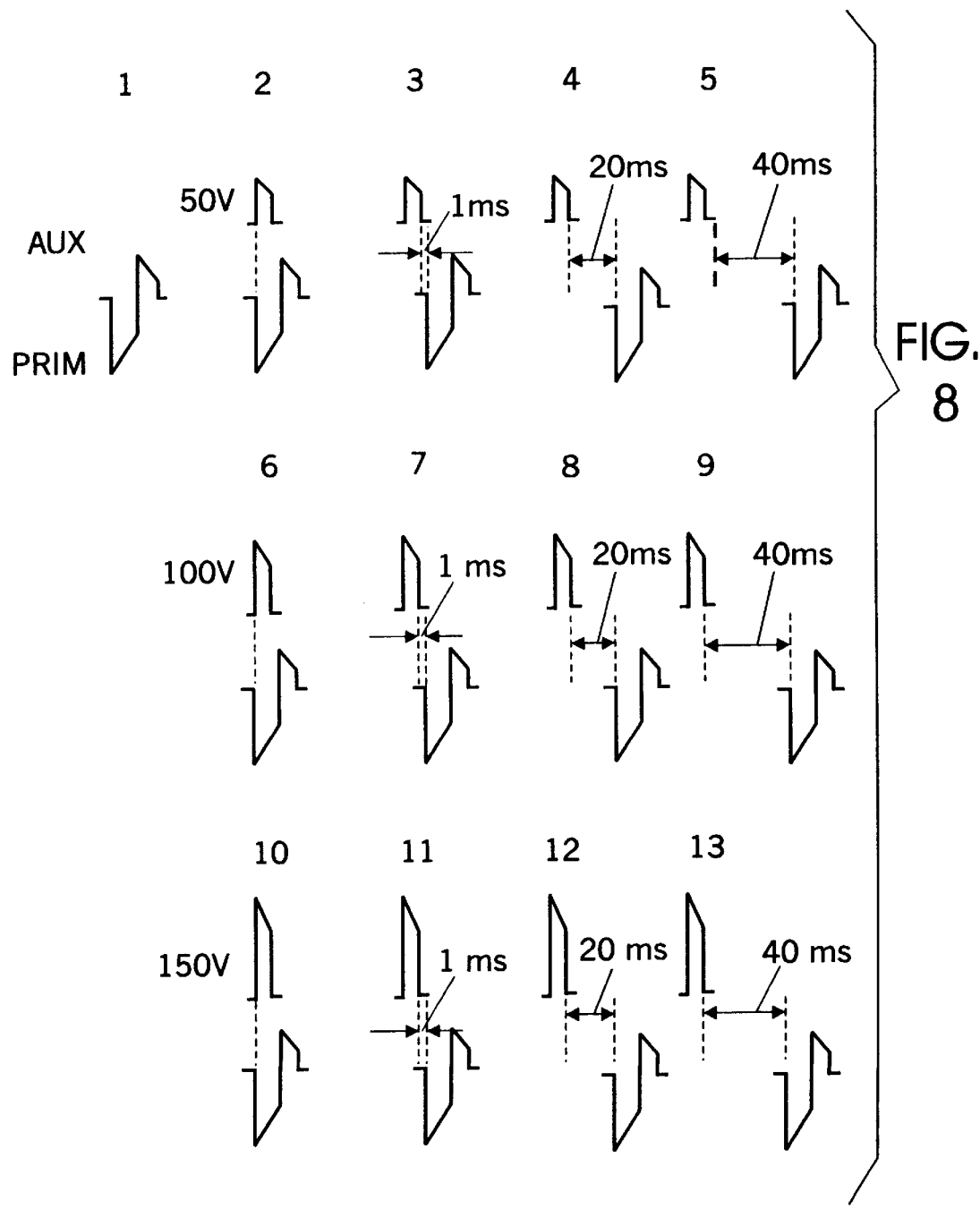
FIG. 8 schematically illustrates the thirteen treatment procedures, including control, used in Example 1 below.

Table 3 below and FIG. 5 illustrate another embodiment of the invention, where the beneficial effects are augmented by placing an additional electrode E; 53 on endocardial transvenous elongate lead 23 in the area of the heart experiencing the weakest electric field when electrode C; 52 is present. The weak field area in this location is in the region of the right ventricular conus. Specifically, the electrode E can be located within the right atrial appendage or the right ventricular outflow track. To accomplish this, the electrode should be located at the most distal portion of the lead body. One configuration for pairing of electrodes in this embodiment is given in Table 3:

TABLE 3

| Electrode Pairings for FIG. 5 | |
| --- | --- |
| Auxiliary Pulse | Primary Pulse |
| C –> E | B –> A + D |

Two embodiments of a suitable transvenous elongate electrode lead 23 are illustrated in FIG. 6, with 6a showing a pace/sense electrode 54 located at the distal tip of the lead 23, while the distal end of the primary electrode 53 is located 10 to 15 millimeters from the top so as to minimize the shock effects on sensing from tissue very near the pace/sense electrode. Sensing of atrial activity is accomplished by measuring the potential difference between the pace/sense electrode 54 and some indifferent electrode such as the shock coil or an electrode away from the heart such as electrode D 16. In the embodiment of 6b, a pair of pace/sense ring electrodes 54, 54' are located proximal to the primary electrode 53. The primary electrode is about 15 to 25 millimeters in length, most preferably 20 millimeters in length, and preferably about 4 to 6 French in diameter, the pair of ring electrodes (2–4 millimeters in length together, with a diameter at least equal to that of the lead body) being positioned 10 to 20 millimeters proximal to the primary electrode. Pacing and sensing capability on lead 23 are particularly important when the system 10 is configured to monitor electrical rhythm activity in both atrial and ventricular chambers.

Table 4 below, taken together with the apparatus of FIG. 3 implementing the waveform of FIG. 4, illustrate three additional configurations of the present invention:

TABLE 4

| Electrode Pairings | |
| --- | --- |
| Auxiliary Pulse | Primary Pulse |
| B –> C | B + C –> A + D |
| C –> D | B + C –> A + D |
| C –> D | B –> C + A + D |

FIG. 7 presents a flow chart schematically illustrating how the electrodes employed to carry out the present invention can be used to modify the therapy delivered. In FIG. 7, electrode C permits sensing of electrical rhythm information and furthermore, allows the implanted device to use that information to select therapy that is tailored to specific rhythm characteristics. In FIG. 7 electrodes C and B are electrically common during sensing and the combined signal is fed into a sensing module for subsequent feature extraction, therapy adaptation in light of the detected feature, and therapy delivery. For example, the time at which the shock is delivered is determined by an algorithm that chooses the optimum time for the defibrillation shock to produce its most significant electrophysiological effects. Other therapy adaptations include the coupling interval between the auxiliary and primary pulses. Several features that could be used alone or in a combined, weighted fashion include mean activation interval, negative and positive slope threshold. In the alternative, rather than electrodes C and D being common, electrograms recorded between electrodes B and C and a common indifferent electrode (electrodes A or D) could be separately fed into the sensing module 60. The feature extraction algorithm can examine features from each electrogram signal alone or in a differential fashion. As previously, the features extracted are then used to guide therapy adaptation and optimize therapy delivery.

Additional embodiments of the present invention are illustrated in Table 5 below, taken in conjunction with the electrode placements illustrated in FIG. 5 and the waveforms presented in FIG. 13, illustrate additional configurations for shocks and electrodes of the present invention.

TABLE 5

| No. | Figure | Primary Pulse | Auxiliary Pulse |
|---|---|---|---|
| 1 | 13a | B -> A + D | C -> A + D |
| 2 | 13a | B -> D | C -> A |
| 3 | 13b | B -> A + D | C -> A + D |
| 4 | 13b | B -> D | C -> A |
| 5 | 13c | B -> A + D | C -> A + D |
| 6 | 13c | B -> D | C -> A |
| 7 | 13d | B -> A + D | C -> A + D |
| 8 | 13d | B -> D | C -> A |

In Table 5, Current flow is indicated by the direction of the arrow from anode (+) to cathode (−). The most preferred configuration is currently Number 5 in Table 5 and FIG. 13C, with a biphasic primary, or defibrillation pulse, followed by a biphasic auxiliary pulse, with the first phase of the auxiliary pulse of opposite polarity from the second phase of the primary pulse, with the primary pulse delivered between a right ventricle electrode B and two electrically common electrodes A and D; and with the auxiliary electrode delivered between the left ventricle electrode C and two eletrically common electrodes A and D.

In alternate embodiments of the invention, the order of the primary pulse and auxiliary pulse for the embodiments set forth in Tables 2 through 5 may be reversed.

Systems as described above may be implanted in a patient by conventional surgical techniques, or techniques readily apparent to skilled surgeons in light of the disclosure provided herein, to provide an implanted defibrillation or cardioversion system.

Additional features can also be added to the invention without affecting the function of the invention and result thereof. Such additional features include, but are not limited to, safety features such as noise suppression or multiple wave monitoring devices (R and T), verification checking to reduce false positive, precardioversion warning, programmed delayed intervention, bipolar configured sensing electrodes, intermittently activated defibrillation detector to reduce energy drain, a switching unit to minimize lines from the pulse generator, etc.

Although the system has been described above as an implantable system, it will be appreciated by those of ordinary skill in the art that the invention could also be incorporated into an external system which employs catheters to position the electrodes for a short time within a patient's heart.

The present invention is explained further in the following non-limiting examples.

EXAMPLE 1

Sub-threshold, Critically-timed,Monophasic Epicardial Pre-shock Significantly Reduces Transvenous Biphasic Defibrillation Threshold in Swine This example shows that the strength and temporal prematurety of the monophasic auxiliary shock significantly affects the strength of the defibrillation threshold of the biphasic primary shock.

Animal model preparation. Domestic farm swine (30–35 kg) were tranquilized via an intramuscular injection of ketamine (20 mg/kg). After about 15 minutes, anesthesia was induced with an intravenous bolus injection of sodium pentobarbital (30 mg/kg) through a 20 gauge needle placed in a prominent ear vein. An endotracheal tube was inserted and the cuff was inflated to provide closed circuit ventilation. Electrocardiographicmonitoring leads were placed on cleaned and shaved portions of the fore limbs and hind limbs. The animal was placed in dorsal recumbence and secured to the table with limb restraints. A deep surgical plane of anesthesia was maintained with continuous intravenous infusion of sodium pentobarbital (0.05 mg/kg/min). Skeletal muscle paralysis was induced with intravenous succinylcholine (1 mg/kg) and maintained with a dosage of 0.25 to 0.50 mg/kg each hour. Additional intravenous injections of sodium pentobarbital (10–20 mg) were given to titrate the anesthesia to an appropriate level. Sterile 0.9% saline solution was infused (2–5 ml/kg/hr) through a central venous catheter placed in an internal jugular vein. A femoral artery was surgically exposed and isolated through an inguinal cutdown. A 4 French polyurethane catheter was inserted and its tip was advanced into the descending aorta. Central arterial pressure was continuously displayed on a monitor (Hewlett Packard Corp.). Anesthesia level was routinely monitored by testing cardiac reflex response to intense pedal pressure, jaw tone and basal heart rate and pressure. Both arterial blood electrolytes ($K^+$, $HCO_3^-$ and $Ca^+$), blood gasses $pO_2$, $pCO_2$) and pH were measured every 30–60 minutes. Abnormal values were corrected by adding electrolytes to the hydration fluids and by adjusting ventilation rate and tidal volume. Esophageal temperature was continuously monitored. Heated water-circulating mats were used to maintain a normothermia(36°–38° C.).

The chest was opened through a median sternotomy. A retractor was installed to improve exposure of the heart and surrounding organs. The pericardium was carefully incised along an axis connecting the base and apex of the heart. A pericardial cradle was fashioned to elevate the heart to a closed-chest position within the chest cavity. Throughout each experiment, the surface of the heart was kept moist and warm by flushing its surface with normal saline and covering the chest cavity with a sheet of plastic.

Defibrillation electrode placement. Four defibrillation electrodes were used in this study; two for the primary shocks and two for the monophasic auxiliary shocks. Defibrillation electrodes mounted on a commercially available lead system (ENDOTAK® model 0094, CPI/Guidant Corp., St. Paul, Minn.) were introduced through a right jugular venotomy. The distal coil electrode (4.0 cm length)

was advanced under fluoroscopic guidance to the right ventricular apex. The proximal coil (6.8 cm length) was positioned with its distal tip 1 to 2 cm cephalid to the junction of the right atrium and superior vena cava using fluoroscopic guidance. The distal and proximal catheter electrodes were used to deliver all the biphasic shocks.

To deliver the monophasic auxiliary shocks, an epicardial electrode formed by concentric ellipses fashioned from platinum coated titanium coils 2 mm in diameter was sutured to the lateral, apical aspect of the left ventricular free wall. This coil-patch electrode circumscribed about 15 $cm^2$ and extended from the apex to about two-thirds the distance from the apex to base. The return electrode, a 6 French titanium coil electrode, 6.8 cm in length, was positioned in the left jugular vein.

After the electrodes were inserted, margins of the incised pericardium were opposed by crossing the cradle tethers and applying gentle traction. The chest retractor was removed, but the chest was not surgically closed. The chest wound was covered with an impermeable plastic drape to keep the heart warm and moist.

Test procedures. The defibrillation threshold was determined in randomized order for each of thirteen experimental treatments in each animal.

Fibrillation. Ventricular fibrillation was induced with 60 Hz alternating current (50–100 mA peak to peak) applied to the pacing tip electrode of the endocardial lead positioned in the right ventricle. In all episodes, fibrillation was allowed to persist for at least 10 seconds but not more than 12 seconds prior to delivery of the defibrillation test shock. When the test failed to defibrillate, the heart was immediately defibrillated with a rescue shock given through the transvenous catheter lead system. The animal was allowed to recover at least four minutes between each test shock.

Defibrillation waveforms. External defibrillators were used to deliver the monophasic and biphasic truncated exponential shocks over two different current pathways. The monophasic shock is referred to as the "auxiliary" pulse and the biphasic shock as the "primary" pulse herein. When delivered simultaneously, the leading edges of both pulses are temporally coincident. When the shocks are given sequentially, the auxiliary primary coupling interval is defined as the time between the trailing edge of the auxiliary pulse and the leading edge of the primary pulse.

All biphasic shocks were delivered by the VENTAK® external cardioverter defibrillator (model 2815, CPI/Guidant Corp., St Paul, Minn). This device delivers shocks having an overall fixed-tilt of 80%. The capacitance is 140 $\mu$F. Total waveform duration varies with shock impedance. Phase one was always 60% of the total duration. Leading edge voltage could be adjusted in 1-volt steps.

The monophasic shocks were delivered by a research defibrillator. The research defibrillator delivers fixed-duration shocks (1–20 ms) with an effective capacitance of 150 $\mu$F. In this study, the monophasic auxiliary pulses were always 5 ms in duration. The initiation of capacitor discharge for both shock generating devices could be externally triggered using a low-amplitude (1–5 volts) pulse. We used a commercially-available current source (Bloom Stimulator, Bloom & Assoc., Reading, Pa.) to generate 1 ms trigger pulses on two independent output channels that were used to control the relative timing between the auxiliary and primary pulses.

The polarity of the defibrillation electrodes was controlled in each experiment since it has been shown that defibrillation can be affected by electrode polarity. The left ventricular electrode was always connected to the anodic terminal (positive) of the defibrillator output circuit, while the right ventricular defibrillation coil electrode was always connected to the cathodic terminal (negative).

Experimental protocol In general, each experiment consisted of multiple episodes of electrically-inducedventricular fibrillation that were intentionally terminated with test shocks. by applying an established set of rules to the observed outcome of each defibrillation trial, shock strengths were selected that permitted the definition of a defibrillation threshold for each experimental treatment. We used the modified Purdue technique to determine defibrillation thresholds. In brief, the strength of the test shock is adjusted according to the outcome (success or failure). The first defibrillation test shock for each treatment in the first animal was 400 V. In all subsequent experiments, the initial test shock strength was adjusted to the mean from the previous animals. If the first test shock failed the next shock voltage was increased 80 V and decreased 80 V if it succeeded. After the first reversal of outcome on successive trials (success to failure or failure to success), the shock strength step was reduced to 40 V. Trials continued until a second outcome reversal was encountered, after which the strength was increased 20 V for a failure and decreased 20 V for a success. The lowest shock strength that defibrillated the ventricles was defined as the defibrillation threshold.

Figure 9:
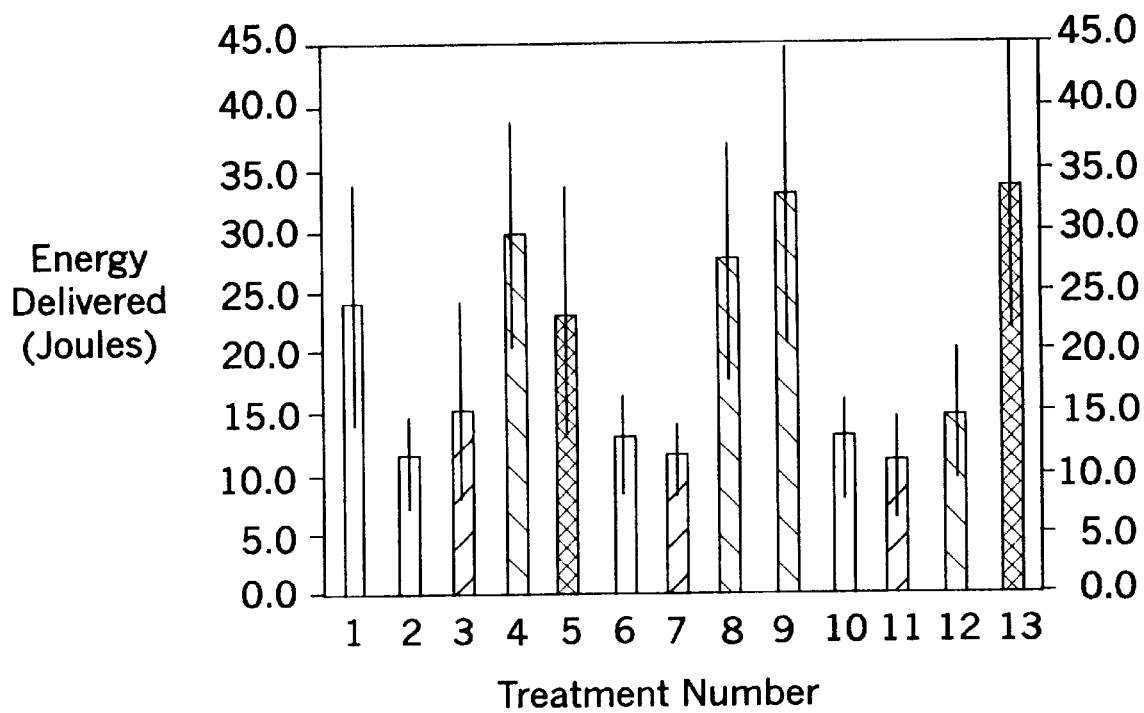
FIG. 9 provides histograms of the mean delivered energy at defibrillation threshold for pulsing schema utilizing auxiliary shocks according to FIG. 8.

In this study, we investigated the influence of two variables on the defibrillation threshold of the primary shock: 1) peak voltage of the auxiliary pulse and 2) auxiliary-primary pulse coupling interval. The primary pulse given alone was used as the control treatment. Three monophasic auxiliary pulse strengths were tested: 50 V, 100 V and 150 V. Each auxiliary pulse strength was tested in combination with an auxiliary-primary pulse coupling interval. Four auxiliary-primary pulse coupling intervals, defined as the time between the trailing edge of the auxiliary pulse and the leading edge of the primary pulse, were tested:—5 ms (simultaneous delivery), 1 ms, 20 ms and 40 ms. The combination of the two variables and the control yields thirteen treatments as shown in FIG. 9. The experimental treatments were tested in randomized order in each animal.

Data acquisition. Defibrillation threshold measurements are more accurate and precise when shock strength measurements are made directly across the defibrillation electrodes. Therefore, the current and voltage during the defibrillation pulses were measured through 4:1 and 200:1 dividers by a waveform analyzer (model 6100, Data Precision, Inc., Danvers, Mass.). The analog current and voltage signals were digitized at 20 kHz and stored in a buffer. The digitized waveforms were displayed after each defibrillation attempt to permit visual inspection. Custom analysis software was used to define the time and amplitude of the leading and trailing edges and to compute the shock impedance and total energy delivered in each pulse. Peak voltage, peak current, shock impedance and energy delivered was recorded for each test shock.

Analysis and results. The mean and standard deviation of peak voltage, peak current, delivered energy and shock impedance for each pulse at defibrillation threshold for each treatment were calculated for the eight animals. For the treatments utilizing an auxiliary pulse, the mean total delivery energy values include the energy delivered in the monophasic pulse. The mean peak current and peak voltage values always reflect the strength of the biphasic primary pulse.

Repeated measures analysis of variance with the Student Newman-Keul's test was used to compare peak voltage, peak current, delivered energy and shock impedance among the treatments. Differences among the means were considered significant when P<0.05. All reported values are mean±SD unless noted otherwise.

The mean energy delivered at defibrillation threshold for each of the experimental treatments is presented in FIG. 9. The mean defibrillation threshold for the control treatment was 24±10.4 J. The defibrillation thresholds were significantly lower (~50%) when a monophasic auxiliary pulse was delivered simultaneously with the biphasic primary pulse. The mean energy delivered in the 50, 100 and 150 V monophasic pulses was 0.09 J, 0.38 J and 0.87 J, respectively. However, there was no significant differences among the simultaneous treatments. Similarly, the defibrillation thresholds for the treatments with a 1 ms auxiliary -primary pulse coupling interval were significantly lower than control, and unlike the simultaneous treatments, there was a trend suggesting that the strength of the monophasic pulse affected the amount of defibrillation threshold reduction.

Figure 10:
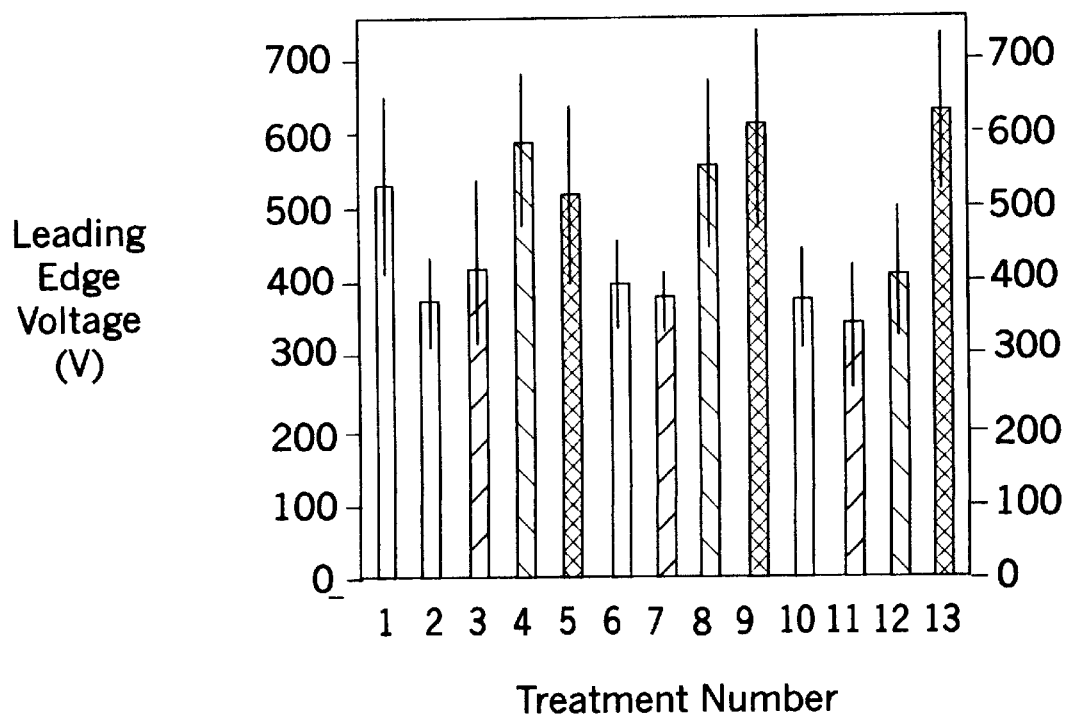
FIG. 10 is similar to FIG. 9 above, except delivered energy is expressed as leading edge voltage rather than in Joules.

Peak voltage requirements at defibrillation threshold followed trends very similar to the trends for energy delivered. FIG. 10 shows mean peak voltage of the primary pulse at defibrillation threshold with and without the auxiliary pulse. When the auxiliary and primary pulses were applied simultaneously, the peak voltage defibrillation threshold was reduced about 25%. For auxiliary-primary coupling intervals of 20 ms and 40 ms, the defibrillation thresholds were not different than control for auxiliary shocks of 50 V and 100 V. However, the defibrillation threshold for the 150 V auxiliary shock with a 20 ms auxiliary-primary coupling interval was significantly lower than the control treatment (P<0.05).

EXAMPLE 2

Single Capacitor Implementation of Dual Shock Defibrillation Method in Closed-Chest Dogs This example demonstrates the feasibility of the dual shock defibrillation therapy demonstrated in Example 1 above with a single capacitor implementation, and with a transvenous lead system.

Animal model preparation. A total of six animals were studied. Methods of preparation were essentially equivalent for each animal. Mixed-breed canines (26–36 kg) were tranquilized via an intramuscular injection of ketamine (10 mg/kg), if necessary. After about 15 minutes, anesthesia was induced with an intravenous bolus injection of sodium pentobarbital (30 mg/kg) through a catheter placed in a cephalic vein. An endotracheal tube was inserted and the cuff was inflated to provide closed circuit ventilation. Electrocardiographic monitoring leads were placed on the cleaned and shaved portions of the fore limbs and hind limbs. The animal was placed in dorsal recumbence and secured to the table with limb restraints. A deep surgical plane of anesthesia was maintained with continuous intravenous infusion of sodium pentobarbital (0.05 mg/kg/min). Skeletal muscle paralysis was induced with intravenous succinylcholine (1 mg/kg) and maintained with a dosage of 0.25 to 0.50 mg/kg each hour.

Additional intravenous injections of sodium pentobarbital (10–20 mg) were given to titrate the anesthesia to an appropriate level prior to performing any surgical procedures. Sterile 0.9% saline solution was infused (2–5 ml/kg/hr) through a central venous catheter placed in an internal jugular vein. A femoral artery was surgically exposed and isolated. A 4 French polyurethane catheter was inserted and its tip was advanced into the descending aorta. Central arterial pressure was continuously displayed on a monitor (Hewlett Packard Corp.). Anesthesia level was routinely monitored by testing cardiac reflex response to intense pedal pressure,jaw tone and basal heart rate and blood pressure. Both arterial blood electrolytes, blood gasses, as well as pH were measured every 30–60 minutes. Abnormal values were corrected by adding electrolytes to the hydration fluids and by adjusting ventilation rate and tidal volume. Esophageal temperature was continuously monitored. Heated water-circulating mats were used to maintain a normothermia (36°–38° C.).

The chest was opened through a median sternotomy. A retractor was installed to improve exposure of the heart and surrounding organs. The pericardium was carefully incised along an axis connecting the base and apex of the heart. A pericardial cradle was fashioned to elevate the heart to a closed-chest position within the chest cavity. When the chest was open during the initial stages of the study, the surface of the heart was kept moist and warm by flushing its surface with normal saline and covering the chest cavity with a sheet of plastic.

Figure 11:
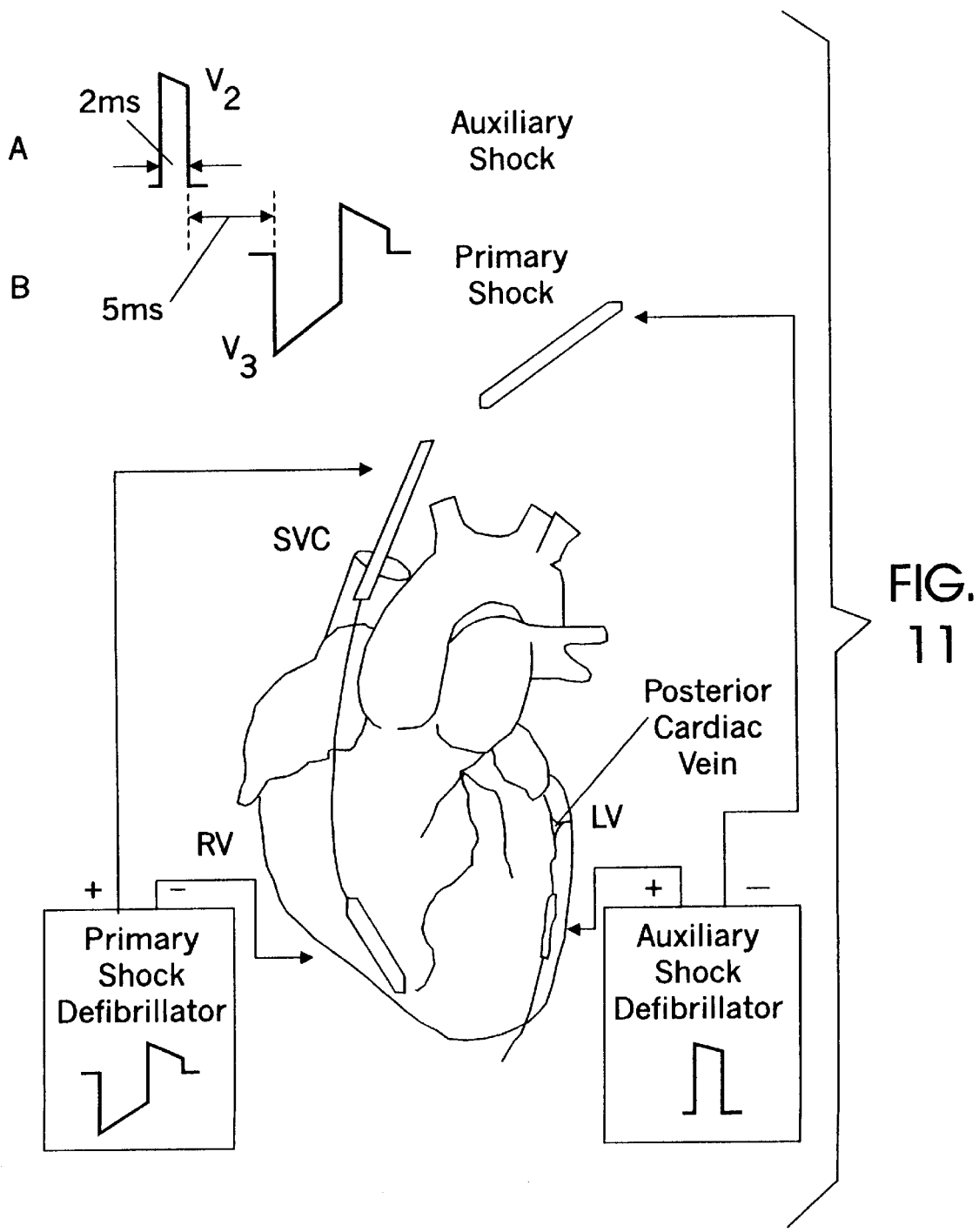
FIGS. 11A and 11B schematically illustrate transvenous electrode placement in the closed-chest dog model described in Example 2 below.

Defibrillation electrode placement. Four defibrillation electrodes were used in this study; two for the primary shocks and two for the monophasic auxiliary shocks (see FIG. 11). Defibrillation electrodes mounted on a commercially available lead system (ENDOTAK® model 0094, CPI/Guidant Corp., St. Paul, Minn.) were introduced through a right jugular venotomy. The distal coil electrode (4.0 cm length) was advanced under fluoroscopic guidance to the right ventricular apex. The proximal coil (6.8 cm length) was positioned with its distal tip 1 to 2 cm cephalid to the junction of the right atrium and superior vena cava using fluoroscopic guidance. The distal and proximal catheter electrodes were used to deliver all the biphasic shocks.

We elected to simulate a transvenous introduction of the left ventricular electrode used to deliver the monophasic auxiliary shocks. The approach was taken because we wanted to control the position of the left ventricular electrode. Closed chest introduction and positioning of the left ventricular electrode using fluoroscopic guidance alone is not trivial. Improper positions could have severely impacted the results of this study. Therefore, efforts were made to simulate a closed-chest model. To accomplish this goal, the left ventricular coil electrode (3 French, 3 cm length, tri-filar platinum coated titanium) was inserted into the posterior cardiac vein. In addition, the chest was closed and evacuated after the left ventricular electrode was positioned. This procedure assured that the volume conductor characteristics of a closed chest were present at the time that defibrillation trials were conducted. The 3 French coil electrode was inserted into the posterior cardiac vein by elevating the apex of the heart to expose the postero-lateral left ventricle. A short segment of an 18 gauge catheter was partially inserted so that about 1 cm was outside the vein. Back flow of venous blood confirmed proper location. The specially designed tip of the defibrillation coil was allowed to engage the catheter which acted as a micro-introducing sheath. Both the introducing catheter and defibrillation electrode were carefully advanced into the vein and secured with a single stitch. this technique was successfully used to position the left ventricular defibrillation electrode within the posterior cardiac vein in all of the six animals.

The return electrode for the monophasic auxiliary shocks, a 6 French titanium coil electrode, 6.8 cm in length, was positioned in the left jugular vein. See FIG. 11.

After the electrodes were inserted, margins of the incised pericardium were opposed by crossing the cradle tethers and applying gentle traction. The chest retractor was removed and the chest was surgically closed in three layers. A chest tube was inserted and continuous suction was applied to evacuate the thoracic cavity.

Test procedures. The defibrillation threshold was determined in randomized order for each of seven experimental treatments in each animal.

Fibrillation. Ventricular fibrillation was induced with 60 Hz alternating current (50–100 mA peak to peak) applied to the pacing tip electrode of the endocardial lead positioned in the right ventricle. In all episodes, fibrillation was allowed to persist for at least 10 seconds but not more than 12 seconds prior to delivery of the defibrillation test shock. When the test failed to defibrillate, the heart was immediately defibrillated with a rescue shock given through the transvenous catheter system. The animal was allowed to recover at least four minutes between each test shock.

Defibrillation waveforms. External defibrillators were used to deliver the monophasic and biphasic truncated exponential shocks over two different current pathways. The monophasic shock is referred to as the "auxiliary" pulse and the biphasic shock as the "primary" pulse herein.

Figure 12:
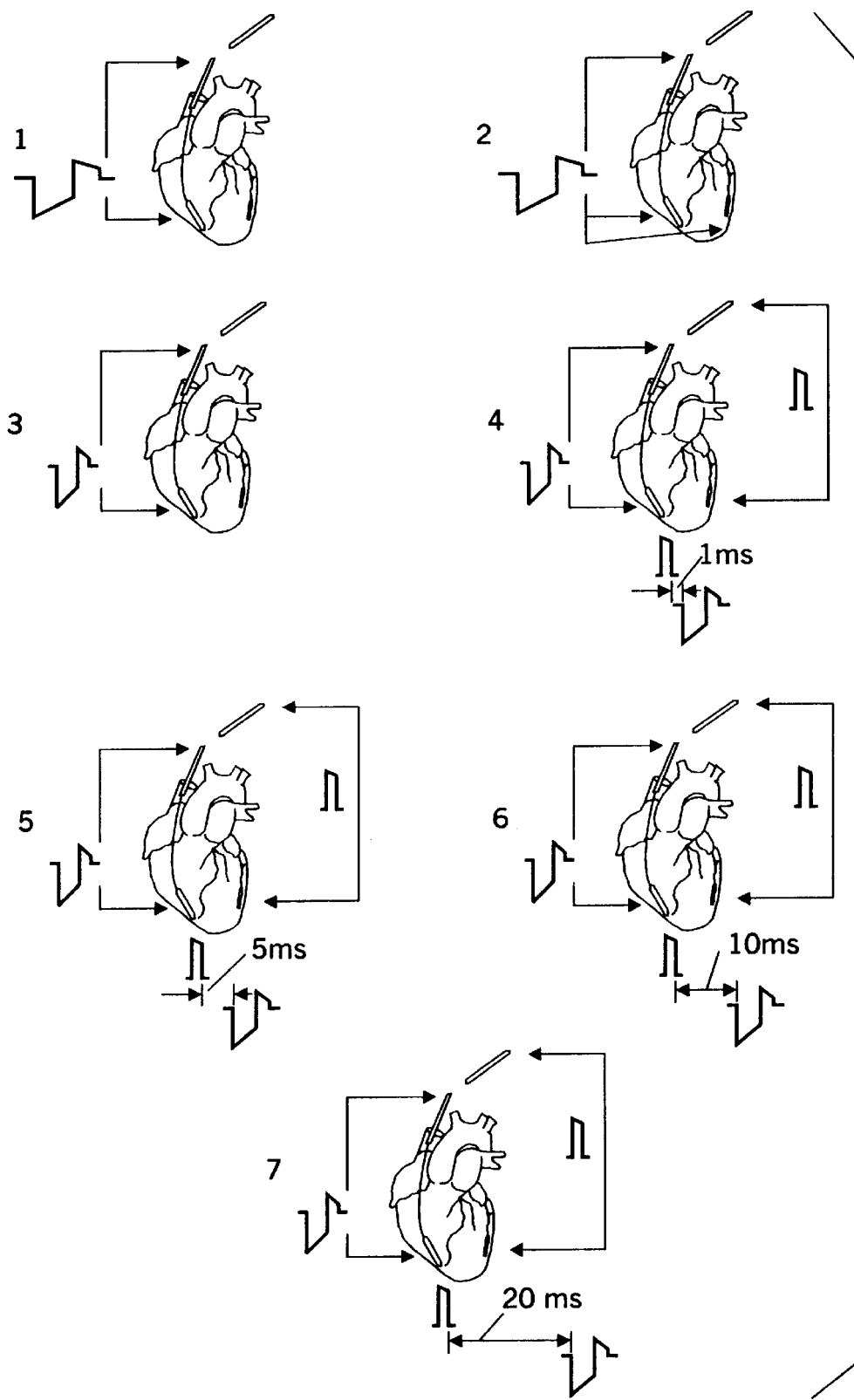
FIG. 12 schematically illustrates seven treatment protocols used in Example 2 below.

Three pulsing schema were tested in this study and are shown in FIG. 12. Unidirectional shocks served as control treatments. Bidirectional and sequential shocks served as the test treatments. Unidirectional shocks were given using the conventional transvenous shock vector (RV→SVC). Bidirectional shocks were applied to electrodes in the shock vector RV+LV→SVC. Sequential shocks were given in a manner similar to that described in the previous chapter. However, in this study the auxiliary-primary coupling interval (defined as the time between the trailing edge of the auxiliary pulse and the leading edge of the primary pulse) tested were 1 ms, 5 ms, 10 ms and 20 ms.

For all sequential shock treatments a single capacitor waveform was emulated. Thus, the trailing edge of the auxiliary pulse was set equal (±10 V) to the leading edge of the primary pulse.

Biphasic primary shocks were delivered by the VEN-TAK® external cardioverter defibrillator as described in Example 1 above or by a research defibrillator. The research defibrillator was programmed to emulate a single capacitor truncated exponential waveform. The first phase duration was 4 ms and the second phase duration was 3 ms. The trailing edge of phase one was equal (±10 V) to the leading edge voltage of phase two.

All of the monophasic shocks were delivered by a research defibrillator. The research defibrillator delivers fixed-duration shocks (1–20 ms) with an effective capacitance of 150 $\mu$F. In this study, the monophasic auxiliary pulses were always 5 ms in duration. The initiation of capacitor discharge for both shock generating devices could be externally triggered using a low-amplitude (1–5 volts) pulse. We used a commercially-available current source (Bloom Stimulator, Bloom & Assoc., Reading, Pa.) to generate 1 ms trigger pulses on two independent output channels that were used to control the relative timing between the auxiliary and primary pulses.

The polarity of the defibrillation electrodes was controlled in each experiment since it has been shown that defibrillation can be affected by electrode polarity. The left ventricular electrode was always connected to the anodic terminal (positive) of the defibrillator output circuit, while the right ventricular defibrillation coil electrode was always connected to the cathodic terminal (negative). When bidirectional shocks were given the left ventricular electrode was connected along with the right ventricular electrode to the cathodic terminal of the external defibrillator.

Experimental protocol In general, each experiment was carried out as described in Example 1 above. The lowest shock strength that defibrillated the ventricles was defined as the defibrillation threshold.

Data acquisition. Data acquisition was carried out in essentially the same manner as described in Example 1 above. Analysis and results. Data analysis was carried out in essentially the same manner as described in Example 1 above.

As shown with reference to FIG. 12 delivered energy requirements at the defibrillation threshold were significantly lower for the dual shock treatments 4, 5, 6 and 7 ($P<0.05$). Differences among the mean energy delivered at the defibrillation threshold for unidirectional shocks (treatments 1 and 3) and bidirectional shocks (treatment 2) were not statistically significant. Additionally, none of the differences among the mean energy delivered at defibrillation threshold for the sequential shocks (treatments 4, 5, 6 and 7) were statistically significant, although there was a strong trend suggesting that the sequential shocks having a 20 ms coupling interval required more energy for defibrillation than sequential shocks having a 1 ms coupling interval (15.4±7.2 J vs. 10.2±4.1 J, $P=0.076$).

EXAMPLE 3

Effect of Varying Preshock and Postshock Tilt on Efficacy of Sequential Waveform Defibrillation Incorporating an LV Electrode In this example, sequential waveform optimization was tested in ten swine using a four-electrode configuration incorporating a left ventricular electrode (LVA). Nine left ventricle (LV) preshock/right ventricle (RV) postshock waveforms were tested, with the tilts of the pre-and post-shocks being varied across a large range (20–60%). TRIAD™ apparatus (available from Guidant Corporation Cardiac Pacemakers (CPI), 4100 Hamline Avenue North, St. Paul, Minn. 55112-5798) and an RV preshock/LV postshock waveform were used as controls.

Methods. The swine were pre-anesthetized with a 2.5 ml IM injection of Telazol, ketamine and xylazine mixture (50 mg/ml tiletamine, 50 mg/ml ketamine, 50 mg/ml xylazine), then were anesthetized with sodium pentothal (50 mg/kg) injected through a cannulated ear vein. They were then intubated with a cuffed endotracheal tube and placed on a ventilator, where then were maintained on an oxygen/isoflurane mixture.

Under fluoroscopy, an ENDOTAK® lead (available from Guidant Corporation Cardiac Pacemakers (CPI))) was inserted via a jugular venotomy into the right ventricle. A subclavicular, subcutaneous pocket was made on the left thorax for insertion of a MINI II "active can" emulator (can). An arterial line was placed in the carotid artory to monitor blood pressure.

A 3 cm DBS electrode was used as the LVA lead in this study. To implant the LVA lead, first a median sternotomy was performed. The exposed pericardium was then incised and the electrode was sutured to the epicardium in a position approximating the path of the lateral coronary vein. The pericardium was then sutured closed. The LVA lead was brought out through the chest wall at the fifth intercostal space. A chest tube was added for drainage. The sternotomy was then closed and the chest evacuated. Fifteen ohms of external resistance was connected to the LVA lead to simulate a prototype LVA lead. The RV vector for preshocks and postshocks was RV→superior vena cava (SVC)+can. The LV vector for preshocks and postshocks was LV→SVC+can. The protocol had eleven test configurations:

1. TRIAD (RV→SVC+can (control))
2. LV preshock, 20% tilt preshock/20% tilt postshock
3. LV preshock, 20% tilt preshock/40% tilt postshock
4. LV preshock, 20% tilt preshock/60% tilt postshock
5. LV preshock, 40% tilt preshock/20% tilt postshock
6. LV preshock, 40% tilt preshock/40% tilt postshock
7. LV preshock, 40% tilt preshock/60% tilt postshock
8. LV preshock, 60% tilt preshock/20% tilt postshock
9. LV preshock, 60% tilt preshock/40% tilt postshock
10. LV preshock, 60% tilt preshock/60% tilt postshock
11. RV preshock, 5 ms fixed duration preshock/40% tilt postshock (control).

Figure 13A:
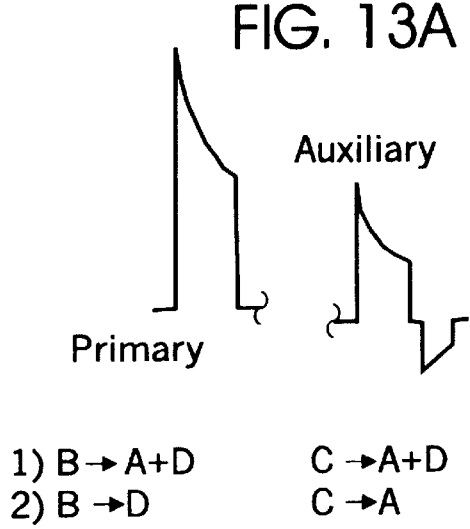
FIG. 13a illustrates a set of waveforms and electrode configurations that may be used to practice the present invention.
Figure 13B:
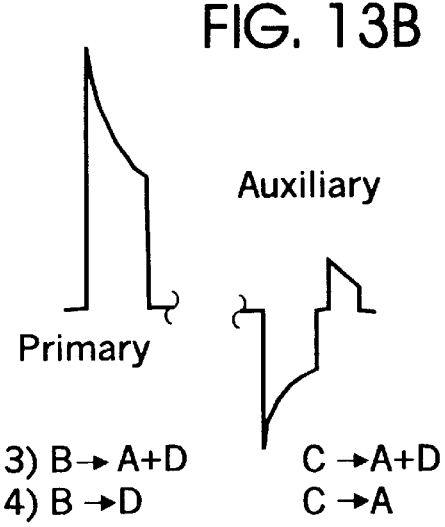
FIG. 13b illustrates a set of waveforms and electrode configurations that may be used to practice the present invention.
Figure 13C:
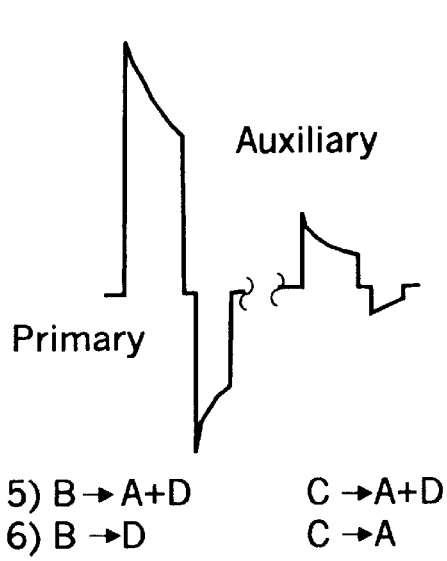
FIG. 13c illustrates a set of waveforms and electrode configurations that may be used to practice the present invention.
Figure 13D:
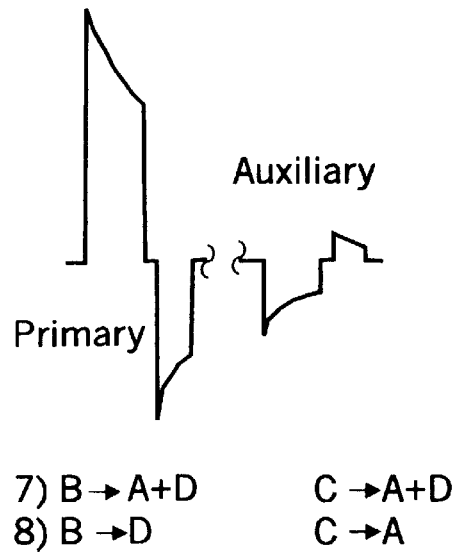
FIG. 13d illustrates a set of waveforms and electrode configurations that may be used to practice the present invention.

The LV preshock test waveforms (numbers 2–10 above) corresponded to the waveform of FIG. 13c number 5 and Table 5 number 5, and were consistently a fixed tilt biphasic, 60:40 duration ratio, truncated exponential preshock, followed by a 5 ms delay, and then a fixed tilt, 60:40 duration ratio, biphasic, truncated exponential postshock. The RV preshock waveform (11) was a 5 ms fixed duration monophasic preshock followed by a 5 ms delay and a 40% fixed tilt, 60:40 biphasic postshock.

Simulated capacitance was 225 ohms for all sequential test configurations. Waveforms were delivered using an AWAG arbitrary waveform generator. Voltage, current and energy data were collected with an automated data collection system.

Fibrillation was induced by two 9 volt batteries placed in series across the shock coils. Fibrillation was confirmed by disorganizationof the surface ECG and loss of blood pressure. Fibrillation was allowed to run ten seconds before a test shock was attempted. In event of a failure, the animal was rescued using a 2815 ECD. Leading edge current of the preshock was increased ten percent after failures, decreased ten percent after success. In either instance, animals were allowed to recover two minutes between fibrillation induction attempts. The up-down procedure was continued until three reversals were observed.

Results. The results are summarized in Table 6 below.

TABLE 6

Preshock voltage, stored and total delivered energies shown for all configurations.

| Configuration | Voltage of First Pulse | Stored Energy | Total Delivered Energy |
|---|---|---|---|
| 1 | 474 ± 20# | 16.0 ± 1.4# | 15.2 ± 1.4# |
| 2 | 321 ± 12* | 11.7 ± 0.9* | 7.3 ± 0.6* |
| 3 | 317 ± 13* | 11.5 ± 0.9* | 9.5 ± 0.8* |
| 4 | 299 ± 12* | 10.2 ± 0.8* | 10.5 ± 0.9* |
| 5 | 354 ± 23* | 14.6 ± 2.1 | 11.3 ± 1.8* |
| 6 | 300 ± 18* | 10.4 ± 1.4* | 9.0 ± 1.2* |
| 7 | 286 ± 7* | 9.2 ± 0.4* | 9.0 ± 0.5* |
| 8 | 442 ± 26# | 22.7 ± 2.6# | 19.0 ± 2.3# |
| 9 | 351 ± 19* | 14.2 ± 1.7* | 12.8 ± 1.7 |
| 10 | 380 ± 27*# | 17.0 ± 2.4*# | 16.6 ± 2.6*# |
| 11 | 311 ± 11* | 11.0 ± 0.8* | 9.1 ± 0.7* |

Values shown as mean ± SEM. * indicates statistically significant versus control group 1. # indicates statistically significant versus control group 11.

Waveforms with lower first shock tilts performed better from a delivered energy standpoint, but not from a voltage and stored energy standpoint. LV preshocks did not noticeably outperform RV preshocks (see number 11 above). The best overall waveform was the 40/40 LV preshock waveform (number 6 above), which had significantly lowered current, voltage and energy as compared to a TRIAD waveform (number 1 above), while still having a low stored energy requirement.

EXAMPLE 4

Effect of Varying Preshock and Postshock Tilt on RV Preshock Dual Waveform Defibrillation Sequential waveform optimization was tested in ten swine using a four-electrode configuration incorporating a left ventricular electrode (LVA). Seven RV preshock/LV postshock waveforms of varying preshock/postshock tilt were tested. Various combinations of preshock/postshock polarities, monophasic/biphasic and biphasic/biphasic preshock/postshock treatments were also tested. A standard TRIAD configuration and an LV preshock/RV postshock waveform were used as control.

Methods. This experiment was carried out in essentially the same manner as in the example immediately above. Again, the RV vector for preshocks and postshocks was RV→SVC+can. The LV vector for preshocks and postshocks was LV→SVC+can. The protocol had nine test configurations:

1. TRIAD (RV→SVC+can (control)
2. RV biphasic (bi) preshock, 40% tilt preshock/20% tilt postshock positive positive;
3. RV bi preshock, 40% tilt preshock 40% tilt postshock positive positive;
4. RV bi preshock, 60% tilt preshock/20% tilt postshock positive positive;
5. RV bi preshock, 60% tilt preshock/40% tilt postshock positive positive;
6. RV bi preshock, 40% tilt preshock/40% tilt postshock positive negative (the first phase of the postshock was in opposite polarity to the first phase of the preshock);
7. RV monophasic (mono) preshock, 40% tilt preshock/ 40% tilt postshock positive negative;
8. RV mono preshock, 40% tilt preshock/40% tilt postshock positive positive;
9. LV bi preshock, 40% tilt preshock/40% tilt postshock positive positive.

Positive indicates a polarity of RV negative→SVC positive+can positive.

Waveforms 2–5 were designed to test the preshock/postshock tilt relationship of RV preshock waveforms. Preshock tilts of 40% and 60% and postshock tilts of 20% and 40% were used. Waveforms 6, 7, and 8, in combination with waveform 3, were designed to study the effect of using a reverse polarity postshock and of using a monophasic or biphasic preshock. Waveform 9, an LV preshock waveform found to be efficacious in the immediately receeding example, was included as an additional control.

Results. The results are summarized in Table 7 below.

TABLE 7

Preshock voltage, stored and total delivered energies shown for all configurations.

| Configuration | Voltage of First Pulse | Stored Energy | Total Delivered Energy |
|---|---|---|---|
| 1 | 512 ± 33# | 19.1 ± 2.4# | 18.5 ± 2.4# |
| 2 | 354 ± 21*# | 14.5 ± 1.6* | 11.1 ± 1.2* |
| 3 | 323 ± 18* | 12.1 ± 1.3* | 10.4 ± 1.1* |
| 4 | 348 ± 18*# | 14.0 ± 1.4* | 12.5 ± 1.3*# |
| 5 | 360 ± 17*# | 14.9 ± 1.4* | 14. ± 1.3*# |
| 6 | 311 ± 16* | 11.1 ± 1.1* | 9.6 ± 1.0* |
| 7 | 298 ± 16* | 10.3 ± 1.1* | 8.6 ± 0.9* |
| 8 | 340 ± 17*^ | 13.3 ± 1.4*^ | 11.5 ± 1.2* |
| 9 | 297 ± 14* | 10.1 ± 0.9* | 8.9 ± 0.8* |

Values shown as mean ± SEM. * indicates statistically significant versus control group 1. # indicates statistically significant versus group 9. ^ indicates significantly different from configuration 7.

All dual shock waveforms performed significantly better than the TRIAD group (1) for delivered energy, voltage and stored energy. 40% tilts for pre- and postshock were efficacious and a good compromise for voltage, current, and energy requirements. Using the RV for the preshock is as effective as using the LV for the same combination of pre and postshock tilt (configurations 3 vs. 9). Biphasic/monophasic preshock did not matter (configurations 2, 3 vs. 7, 8). Relative polarity of the pre and postshock matters for the monophasic preshock (configurations 7 vs. 8) but not for biphasic (configurations 3 vs. 6). Configuration 6 is currently most preferred.

The foregoing is illustrative of the present invention, and is not to be construed as limiting thereof. The invention is defined by the following claims, with equivalents of the claims to be included therein.

That which is claimed is:

1. An implantable system for the defibrillation or cardioversion of the heart of a patient in need of such treatment, said system comprising:
   a primary electrodes configured for delivering a defibrillation pulse along a predetermined current pathway in a first portion of said heart, said current pathway defining a weak field area in a second portion of said heart;
   at least one auxiliary electrode configured for delivering an auxiliary pulse to said weak field area;
   a power supply; and
   a control circuit operatively associated with said primary electrodes, said auxiliary electrode, and said power supply, said control circuit configured for delivering a cardioversion sequence comprising an auxiliary pulse sufficient to induce a cessation of propagation in said weak field area through said auxiliary electrode, followed by a defibrillation pulse through said primary electrodes delivered during said cessation of propagation in said weak field area;
   wherein said control circuit is configured to deliver a biphasic auxiliary pulse and a biphasic defibrillation pulse, with the first phase of said defibrillation pulse in opposite polarity to said auxiliary pulse.

2. A system according to claim 1, wherein said control circuit is configured so that a trailing edge voltage of said auxiliary pulse is equal to a leading edge voltage of said defibrillation pulse.

3. A system according to claim 1, wherein said control circuit is configured to deliver a monophasic auxiliary pulse of from 0.5 to 10 milliseconds in duration.

4. A system according to claim 1, wherein said control circuit is configured to deliver said defibrillation pulse within 20 milliseconds after said auxiliary pulse.

5. A system according to claim 1, wherein said at least one auxiliary electrode is configured for positioning through the coronary sinus and in either the apical third of the posterior cardiac vein or the apical half of the great cardiac vein.

6. A system according to claim 1, wherein each of said at least one auxiliary electrode is carried by a transvenous lead.

7. A system according to claim 1, wherein said power supply includes a capacitor.

8. A system according to claim 1, wherein said power supply includes a single capacitor, and wherein said control circuit is configured so that both said auxiliary pulse and said defibrillation pulse are generated by the discharge of said single capacitor.

9. A system according to claim 1, wherein said power supply includes a first and second capacitor, and wherein said control circuit is configured so that said auxiliary pulse is generated by the discharge of said first capacitor and said defibrillation pulse is generated by the discharge of said second capacitor.

10. A system according to claim 1, wherein said power supply includes a first and second capacitor, and wherein said control circuit is configured so that said auxiliary pulse is generated by the discharge of said first and second capacitors, and said defibrillation pulse is generated by the discharge of said first and second capacitors.

11. A system according to claim 1, wherein said control circuit is configured so that said auxiliary pulse is not more than 50% of the peak current and not more than 30% of the delivered energy of said defibrillation pulse.

12. An implantable system for the defibrillation of the ventricles of the heart of a patient in need of such treatment, said system comprising:
   a plurality of primary electrodes configured for delivering a defibrillation pulse along a predetermined current pathway in a first portion of said heart, said current pathway defining a weak field area in a second portion of said heart;
   at least one auxiliary electrode configured for delivering an auxiliary pulse to said weak field area, with said at least one auxiliary electrode configured for positioning through the coronary sinus and in a vein on the surface of the left ventricle of said heart;
   a power supply; and
   a control circuit operatively associated with said primary electrodes, said at least one auxiliary electrode, and said power supply, said control circuit configured for delivering a cardioversion sequence comprising a biphasic auxiliary pulse through said auxiliary electrode, followed by a biphasic defibrillation pulse through said primary electrodes, with said defibrillation pulse delivered within 20 milliseconds after said auxiliary pulse, and with the first phase of said defibrillation pulse in opposite polarity to said auxiliary pulse.

13. A system according to claim 12, wherein said control circuit is configured so that a trailing edge voltage of said auxiliary pulse is equal to a leading edge voltage of said defibrillation pulse.

14. A system according to claim 12, comprising:
   a first primary electrode configured for positioning in the superior vena cava or innominate vein; and
   a second primary electrode configured for positioning in the right ventricle.

15. A system according to claim 14, wherein said first and second primary electrodes are carried by a common transvenous lead.

16. A system according to claim 12, comprising:
a first primary electrode configured for positioning in the superior vena cava or innominate vein;
a second primary electrode configured for positioning in the right ventricle; and
a second auxiliary electrode positioned near the right ventricular conus;
with said control circuit configured for delivering said monophasic auxiliary pulse through said first and second auxiliary electrodes.

17. A system according to claim 16, with said second auxiliary electrode configured for positioning in the anterior portion of the right atrial appendage or in the right ventricular outflow track.

18. A system according to claim 16, wherein said second auxiliary electrode is carried by a transvenous lead, and wherein said second auxiliary electrode is positioned on the distal end of said transvenous lead.

19. A system according to claim 16, wherein said first and second primary electrodes are carried by a common transvenous lead.

20. A system according to claim 12, wherein said power supply includes a single capacitor, and wherein said control circuit is configured so that both said auxiliary pulse and said defibrillation pulse are generated by the discharge of said single capacitor.

21. A system according to claim 12, wherein said power supply includes a first and second capacitor, and wherein said control circuit is configured so that said auxiliary pulse is generated by the discharge of said first capacitor and said defibrillation pulse is generated by the discharge of said second capacitor.

22. A system according to claim 12, wherein said power supply includes a first and second capacitor, and wherein said control circuit is configured so that said auxiliary pulse is generated by the discharge of said first and second capacitors, and said defibrillation pulse is generated by the discharge of said first and second capacitors.

23. An implantable system for the defibrillation or cardioversion of the heart of a patient in need of such treatment, said system comprising:
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area;
a power supply; and
a control circuit operatively associated with said primary electrodes, said auxiliary electrode, and said power supply, said control circuit configured for delivering a cardioversion sequence comprising a defibrillation pulse through said primary electrodes, followed by an auxiliary pulse sufficient to induce a cessation of propagation in said weak field area through said auxiliary electrode;
wherein said control circuit is configured to deliver a biphasic auxiliary pulse and a biphasic defrillation pulse; and wherein said control circuit is configured so that a leading edge voltage of said auxiliary pulse is equal to a trailing edge voltage of said defibrillation pulse.

24. A system according to claim 23, wherein said control circuit is configured to deliver a monophasic auxiliary pulse of from 0.5 to 10 milliseconds in duration.

25. A system according to claim 23, wherein said control circuit is configured to deliver said defibrillation pulse within 20 milliseconds after said auxiliary pulse.

26. A system according to claim 23, wherein said at least one auxiliary electrode is configured for positioning through the coronary sinus and in a vein on the surface of the left ventricle of said heart.

27. A system according to claim 23, wherein said at least one auxiliary electrode is configured for positioning through the coronary sinus and in either the apical third of the posterior cardiac vein or the apical half of the great cardiac vein.

28. A system according to claim 23, wherein each of said plurality of primary electrodes is carried by a transvenous lead.

29. A system according to claim 23, wherein each of said at least one auxiliary electrode is carried by a transvenous lead.

30. A system according to claim 23, wherein said power supply includes a capacitor.

31. A system according to claim 23, wherein said power supply includes a single capacitor, and wherein said control circuit is configured so that both said auxiliary pulse and said defibrillation pulse are generated by the discharge of said single capacitor.

32. A system according to claim 23, wherein said power supply includes a first and second capacitor, and wherein said control circuit is configured so that said auxiliary pulse is generated by the discharge of said first capacitor and said defibrillation pulse is generated by the discharge of said second capacitor.

33. A system according to claim 23, wherein said power supply includes a first and second capacitor, and wherein said control circuit is configured so that said auxiliary pulse is generated by the discharge of said first and second capacitors, and said defibrillation pulse is generated by the discharge of said first and second capacitors.

34. An implantable system for the defibrillation of the ventricles of the heart of a patient in need of such treatment, said system comprising:
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area, with said at least one auxiliary electrode configured for positioning through the coronary sinus and in a vein on the surface of the left ventricle of said heart;
a power supply; and
a control circuit operatively associated with said primary electrodes, said at least one auxiliary electrode, and said power supply, said control circuit configured for delivering a cardioversion sequence comprising a biphasic defibrillation pulse through said primary electrodes followed by a biphasic auxiliary pulse through said auxiliary electrode, with said auxiliary pulse delivered within 20 milliseconds after said auxiliary pulse, and with the first phase of said defibrillation pulse in opposite polarity to said auxiliary pulse; wherein said system further comprises
a first primary electrode configured for positioning in the superior vena cava or innominate vein;
a second primary electrode configured for positioning in the right ventricle; and
a second auxiliary electroden positioning near the right ventricular conus;

with said control circuit configured for delivering said monophasic auxiliary pulse through said first and second auxiliary electrode.

35. A system according to claim 34, wherein said control circuit is configured so that a leading edge voltage of said auxiliary pulse is equal to a trailing edge voltage of said defibrillation pulse.

36. A system according to claim 34, with said second auxiliary electrode configured for positioning in the anterior portion of the right atrial appendage or in the right ventricular outflow track.

37. A system according to claim 34, wherein said second auxiliary electrode is carried by a transvenous lead, and wherein said second auxiliary electrode is positioned on the distal end of said transvenous lead.

38. A system according to claim 34, wherein said first and second primary electrodes are carried by a common transvenous lead.

39. A system according to claim 34, wherein said power supply includes a single capacitor, and wherein said control circuit is configured so that both said auxiliary pulse and said defibrillation pulse are generated by the discharge of said single capacitor.

40. A system according to claim 34, wherein said power supply includes a first and second capacitor, and wherein said control circuit is configured so that said auxiliary pulse is generated by the discharge of said first capacitor and said defibrillation pulse is generated by the discharge of said second capacitor.

41. A system according to claim 34, wherein said power supply includes a first and second capacitor, and wherein said control circuit is configured so that said auxiliary pulse is generated by the discharge of said first and second capacitors, and said defibrillation pulse is generated by the discharge of said first and second capacitors.

42. An electrode lead useful for the cardioversion or defibrillation of a patient's heart, comprising:

an elongate transvencous electrode lead having a distal end portion, with said lead configured for positioning said distal end portion within the right atrial appendage; and a primary electrode connected to said electrode lead and positioned on said distal end portion;

further comprising a secondary pace/sense electrode connected to said electrode lead at said distal end portion;

wherein said secondary pace/sense electrode is connected to said electrode lead in a position proximal to said electrode.

43. An electrode lead according to claim 42, wherein said secondary pace/sense electrode comprises a pair of ring electrodes.

44. An implantable system for the defibrillation of the ventricles of the heart of a patient in need of such treatment, said system comprising:

a plurality of primary electrodes configured for delivering a defibrillation pulse along a predetermined current pathway in a first portion of said heart, said current pathway defining a weak field area in a second portion of said heart, said plurality of primary electrodes including an electrode configured for positioning in the right ventricle;

at least one auxiliary electrode configured for delivering an auxiliary pulse to said weak field area, with said at least one auxiliary electrode configured for positioning through the coronary sinus and in a vein on the surface of the left ventricle of said heart;

a power supply; and a control circuit operatively associated with said primary electrodes, said at least one auxiliary electrode, and said power supply, said control circuit configured for delivering a cardioversion sequence comprising a biphasic defibrillation pulse through said primary electrodes followed by a biphasic auxiliary pulse through said auxiliary electrode, with said auxiliary pulse delivered within 20 milliseconds after said defibrillation pulse, and with the first phase of said defibrillation pulse in opposite polarity to said auxiliary pulse.

45. A system according to claim 44, further comprising a housing configured for being implanted in the left thoracic region of said patient, said housing containing said power supply and said control circuit, and with said housing having an active external portion serving as a second primary electrode.

46. A system according to claim 45, wherein said auxiliary pulse is delivered between said auxiliary electrode and said second primary electrode.

47. A system according to claim 44, further comprising a second primary electrode configured for positioning in the superior vena cava or innominate vein.

48. A system according to claim 47, wherein said auxiliary pulse is delivered between said auxiliary electrode and said second primary electrode.

49. A system according to claim 44, further comprising:

a housing configured for being implanted in the left thoracic region of said patient, said housing containing said power supply and said control circuit, and with said housing having an active external portion serving as a second primary electrode; and a third primary electrode configured for positioning in the superior vena cava or innominate vein;

wherein said second and third primary electrodes are electrically common.

50. A system according to claim 49, wherein said auxiliary pulse is delivered between said auxiliary electrode, and said second and third electrically common primary electrodes.

51. A system according to claim 44, wherein said control circuit is configured so that a leading edge voltage of said auxiliary pulse is equal to a trailing edge voltage of said defibrillation pulse.

52. An implantable system for the defibrillation of the ventricles of the heart of a patient in need of such treatment, said system comprising:

a plurality of primary electrodes configured for delivering a defibrillation pulse along a predetermined current pathway in a first portion of said heart, said current pathway defining a weak field area in a second portion of said heart, said plurality of primary electrodes including an electrode configured for positioning in the right ventricle;

at least one auxiliary electrode configured for delivering an auxiliary pulse to said weak field area, with said at least one auxiliary electrode configured for positioning through the coronary sinus and in a vein on the surface of the left ventricle of said heart;

a power supply; and a control circuit operatively associated with said primary electrodes, said at least one auxiliary electrode, and said power supply, said control circuit configured for delivering a cardioversion sequence comprising an auxiliary pulse through said auxiliary electrode followed by a biphasic defibrillation pulse through said primary electrodes, with said defibrillation pulse delivered within 20 milliseconds after said auxiliary pulse, and with the first phase of said defibrillation pulse in opposite polarity to said auxiliary pulse;

further comprising a housing configured for being implanted in the left thoracic region of said patient, said housing containing said power supply and said control circuit and with said housing having an active external portion serving as a second primary electrode.

53. A system according to claim 52, wherein said auxiliary pulse is delivered between said auxiliary electrode and said second primary electrode.

54. A system according to claim 52, wherein said control circuit is configured so that a leading edge voltage of said auxiliary pulse is equal to a trailing edge voltage of said defibrillation pulse.

55. An implantable defibrillator, comprising:
a housing;
a power supply contained within said housing, with said power supply including a storage capacitor; and
a control circuit contained within said housing and operatively associated with said power supply, said control circuit configured for delivering a cardioversion sequence comprising an auxiliary pulse and a defibrillation pulse;
said housing having a volume less than 35 cubic centimeters.

56. An implantable defibrillator according to claim 55, said power supply further comprising a battery.

57. An implantable defibrillator according to claim 55, wherein said control circuit is configured so that said defibrillation pulse follows said auxiliary pulse, and so that a trailing edge voltage of said auxiliary pulse is equal to a leading edge voltage of said defibrillation pulse.

58. An implantable defibrillator according to claim 55, wherein said control circuit is configured so tat said auxiliary pulse follows said defibrillation pulse, and so that a trailing edge voltage of said defibrillation pulse is equal to a leading edge voltage of said auxiliary pulse.

59. An implantable defibrillator according to claim 55, said housing having a volume of at least 5 cubic centimeters.

60. An implantable system for the defibrillation or cardioversion of the heart of a patient in need of such treatment, said system comprising:
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area;
a power supply; and
a control circuit operatively associated with said primary electrodes, said auxiliary electrode, and said power supply, said control circuit configured for delivering a cardioversion sequence comprising an auxiliary pulse sufficient to induce a cessation of propagation in said weak field area through said auxiliary electrode, followed by a defibrillation pulse through said primary electrodes delivered during said cessation of propagation in said weak field area;
wherein said at least one auxiliary electrode is configured for positioning through the coronary sinus and in a vein on the surface of the left ventricle of said heart.

61. An implantable system for the defibrillation or cardioversion of the heart of a patient in need of such treatment, said system comprising:
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area;
a power supply; and
a control circuit operatively associated with said primary electrodes, said auxiliary electrode, and said power supply, said control circuit configured for delivering a cardioversion sequence comprising an auxiliary pulse sufficient to induce a cessation of propagation in said weak field area through said auxiliary electrode, followed by a defibrillation pulse through said primary electrodes delivered during said cessation of propagation in said weak field area;
wherein said at least one auxiliary electrode is configured for positioning through the coronary sinus and in a vein on the postero-lateral surface of the left ventricle of said heart.

62. An implantable system for the defibrillation or cardioversion of the heart of a patient in need of such treatment, said system comprising;
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area;
a power supply; and
a control circuit operatively associated with said primary electrodes, said auxiliary electrode, and said power supply, said control circuit configured for delivering a cardioversion sequence comprising an auxiliary pulse sufficient to induce a cessation of propagation in said weak field area through said auxiliary electrode, followed by a defibrillation pulse through said primary electrodes delivered during said cessation of propagation in said weak field area;
wherein each of said plurality of primary electrodes is carried by a transvenous lead.

63. An implantable system for the defibrillation or cardioversion of the heart of a patient in need of such treatment, said system comprising:
a plurality of primary electrodes configured for delivering a defibrillation pulse along a predetermined current pathway in a first portion of said heart, said current pathway defining a weak field area in a second portion of said heart;
at least one auxiliary electrode configured for delivering an auxiliary pulse to said weak field area;
a power supply; and
a control circuit operatively associated with said primary electrodes, said auxiliary electrode, and said power supply, said control circuit configured for delivering a cardioversion sequence comprising an auxiliary pulse sufficient to induce a cessation of propagation in said weak field area through said auxiliary electrode, followed by a defibrillation pulse through said primary electrodes delivered during said cessation of propagation in said weak field area;

wherein said power supply includes a 20 to 400 microfarad capacitor.

64. An implantable system for the defibrillation or cardioversion of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area;
 a power supply; and
 a control circuit operatively associated with said primary electrodes, said auxiliary electrode, and said power supply, said control circuit configured for delivering a cardioversion sequence comprising a defibrillation pulse through said primary electrodes, followed by an auxiliary pulse sufficient to induce a cessation of propagation in said weak field area through said auxiliary electrode;
 wherein said control circuit is configured to deliver a monophasic auxiliary pulse of from 0.5 to 10 milliseconds in duration.

65. An implantable system for the defibrillation or cardioversion of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area;
 a power supply; and
 a control circuit operatively associated with said primary electrodes, said auxiliary electrode, and said power supply, said control circuit configured for delivering a cardioversion sequence comprising a defibrillation pulse through said primary electrodes, followed by an auxiliary pulse sufficient to induce a cessation of propagation in said weak field area through said auxiliary electrode;
 wherein said at least one auxiliary electrode is configured for positioning through the coronary sinus and in a vein on the postero lateral surface of the left ventricle of said heart.

66. An implantable system for the defibrillation or cardioversion of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area;
 a power supply; and
 a control circuit operatively associated with said primary electrodes, said auxiliary electrode, and said power supply, said control circuit configured for delivering a cardioversion sequence comprising a defibrillation pulse through said primary electrodes, followed by an auxiliary pulse sufficient to induce a cessation of propagation in said weak field area through said auxiliary electrode;

wherein said power supply includes a 20 to 400 microfarad capacitor.

67. An implantable system for the defibrillation or cardioversion of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area;
 a power supply; and
 a control circuit operatively associated with said primary electrodes, said auxiliary electrode, and said power supply, said control circuit configured for delivering a cardioversion sequence comprising a defibrillation pulse through said primary electrodes, followed by an auxiliary pulse sufficient to induce a cessation of propagation in said weak field area through said auxiliary electrode;
 wherein said control circuit is configured so that said auxiliary pulse is not more than 50% of the peak current and not more than 30% of the delivered energy of said defibrillation pulse.

68. An implantable system for the defibrillation of the ventricles of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area, with said at least one auxiliary electrode configured for positioning through the coronary sinus and in a vein on the surface of the left ventricle of said heart;
 a power supply; and
 a control circuit operatively associated with said primary electrodes, said at least one auxiliary electrode, and said power supply, said control circuit configured for delivering a cardioversion sequence comprising a biphasic defibrillation pulse through said primary electrodes followed by a biphasic auxiliary pulse through said auxiliary electrode, with said auxiliary pulse delivered within 20 milliseconds after said auxiliary pulse, and with the first phase of said defibrillation pulse in opposite polarity to said auxiliary pulse; said system comprising
 a first primary electrode configured for positioning in the superior vena cava or innominate vein; and
 a second primary electrode configured for positioning in the right ventricle.

69. An implantable system for the defibrillation of the ventricles of the heart of a patient in need of such treatment, said system comprising:
 a plurality of primary electrodes configured for delivering a defibrillation pulse along a predetermined current pathway in a first portion of said heart, said current pathway defining a weak field area in a second portion of said heart;
 at least one auxiliary electrode configured for delivering an auxiliary pulse to said weak field area, with said at least one auxiliary electrode configured for positioning through the coronary sinus and in a vein on the surface of the left ventricle of said heart;

a power supply; and a control circuit operatively associated with said primary electrodes, said at least one auxiliary electrode, and said power supply, said control circuit configured for delivering a cardioversion sequence comprising a biphasic defibrillation pulse through said primary electrodes followed by a biphasic auxiliary pulse through said auxiliary electrode, with said auxiliary pulse delivered within 20 milliseconds after said auxiliary pulse, and with the first phase of said defibrillation pulse in opposite polarity to said auxiliary pulse.

70. An implantable system according to claim 69, wherein said first and second primary electrodes are carried by a common transvenous lead.

71. An implantable system for the defibrillation of the ventricles of the heart of a patient in need of such treatment, said system comprising:

a plurality of primary electrodes configured for delivering a defibrillation pulse along a predetermined current pathway in a first portion of said heart, said current pathway defining a weak field area in a second portion of said heart, said plurality of primary electrodes including an electrode configured for positioning in the right ventricle;

at least one auxiliary electrode configured for delivering an auxiliary pulse to said weak field area, with said at least one auxiliary electrode configured for positioning through the coronary sinus and in a vein on the surface of the left ventricle of said heart;

a power supply; and a control circuit operatively associated with said primary electrodes, said at least one auxiliary electrode, and said power supply, said control circuit configured for delivering a cardioversion sequence comprising an auxiliary pulse through said auxiliary electrode followed by a biphasic defibrillation pulse through said primary electrodes, with said defibrillation pulse delivered within 20 milliseconds after said auxiliary pulse, and with the first phase of said defibrillation pulse in opposite polarity to said auxiliary pulse;

further comprising a second primary electrode configured for positioning in the superior vena cava or innominate vein.

72. A system according to claim 71, wherein said auxiliary pulse is delivered between said auxiliary electrode and said second primary electrode.

73. An implantable system for the defibrillation of the ventricles of the heart of a patient in need of such treatment, said system comprising:

a plurality of primary electrodes configured for delivering a defibrillation pulse along a predetermined current pathway in a first portion of said heart, said current pathway defining a weak field area in a second portion of said heart, said plurality of primary electrodes including an electrode configured for positioning in the right ventricle;

at least one auxiliary electrode configured for delivering an auxiliary pulse to said weak field area, with said at least one auxiliary electrode configured for positioning through the coronary sinus and in a vein on the surface of the left ventricle of said heart;

a power supply; and a control circuit operatively associated with said primary electrodes, said at least one auxiliary electrode, and said power supply, said control circuit configured for delivering a cardioversion sequence comprising an auxiliary pulse through said auxiliary electrode followed by a biphasic defibrillation pulse through said primary electrodes, with said defibrillation pulse delivered within 20 milliseconds after said auxiliary pulse, and with the first phase of said defibrillation pulse in opposite polarity to said auxiliary pulse, said system further comprising:

a housing configured for being implanted in the left thoracic region of said patient, said housing containing said power supply and said control circuit, and with said housing having an active external portion serving as a second primary electrode; and a third primary electrode configured for positioning in the superior vena cava or innominate vein;

wherein said second and third primary electrodes are electrically common.

74. A system according to claim 73, wherein said auxiliary pulse is delivered between said auxiliary electrode, and said second and third electrically common primary electrodes.

* * * * *

UNITED STATES PATENT AND TRADEMARK OFFICE
CERTIFICATE OF CORRECTION

PATENT NO. : 5,978,705

DATED : November 2, 1999

INVENTOR(S) : Bruce H. KenKnight, Raymond E. Ideker; Robert S. Booker, III and Stephen J. Hahn It is certified that error appears in the above-identified patent and that said Letters Patent is hereby corrected as shown below:

Column 21, Line 39, insert --plurality of-- before "primary"

Column 24, Line 66, delete "electroden" and insert --electrode--.

Column 24, Line 66, delete "positioning" and insert --positioned--.

Signed and Sealed this

Twenty-fourth Day of April, 2001

Attest:

NICHOLAS P. GODICI

Attesting Officer

Acting Director of the United States Patent and Trademark Office